US009348969B2

(12) United States Patent
Alsanousi

(10) Patent No.: US 9,348,969 B2
(45) Date of Patent: May 24, 2016

(54) SYSTEM AND METHOD FOR PERSONALIZED BIOMEDICAL INFORMATION RESEARCH ANALYTICS AND KNOWLEDGE DISCOVERY

(71) Applicant: Ali Alsanousi, Boston, MA (US)

(72) Inventor: Ali Alsanousi, Boston, MA (US)

( * ) Notice: Subject to any disclaimer, the term of this patent is extended or adjusted under 35 U.S.C. 154(b) by 406 days.

(21) Appl. No.: 13/934,651

(22) Filed: Jul. 3, 2013

(65) Prior Publication Data
US 2015/0012482 A1    Jan. 8, 2015

(51) Int. Cl.
| | |
|---|---|
| *G06F 7/00* | (2006.01) |
| *G06F 17/00* | (2006.01) |
| *G06F 19/24* | (2011.01) |
| *G06F 19/28* | (2011.01) |
| *G06F 19/00* | (2011.01) |
| *G06F 19/18* | (2011.01) |

(52) U.S. Cl.
CPC .............. *G06F 19/24* (2013.01); *G06F 19/28* (2013.01); *G06F 19/322* (2013.01); *G06F 19/3443* (2013.01); *G06F 19/18* (2013.01)

(58) Field of Classification Search
CPC ... G06F 19/24; G06F 19/3443; G06F 19/322; G06F 19/28; G06F 19/18; G06F 17/30592; G06F 17/30575; G06F 17/30286; G06F 17/30578; G06F 17/3071; G06Q 10/06; G06Q 30/02
See application file for complete search history.

(56) References Cited

U.S. PATENT DOCUMENTS

| | | | |
|---|---|---|---|
| 7,418,399 B2 | 8/2008 | Schaeffer et al. | |
| 2007/0038706 A1 | 2/2007 | Karamchedu et al. | |
| 2008/0147554 A1* | 6/2008 | Stevens | G06F 19/322 705/51 |
| 2010/0217094 A1 | 8/2010 | Seward | |
| 2011/0166890 A1 | 7/2011 | Menschik et al. | |
| 2012/0205453 A1* | 8/2012 | Rampersad | G06Q 50/26 235/494 |
| 2013/0144887 A1* | 6/2013 | Chen | G06F 19/3456 707/748 |
| 2013/0268290 A1* | 10/2013 | Jackson | G06F 19/28 705/2 |

* cited by examiner

*Primary Examiner* — Azam Cheema
(74) *Attorney, Agent, or Firm* — Oblon, McClelland, Maier & Neustadt, L.L.P.

(57) ABSTRACT

A Health Information Virtual Exchange (HIVE) BIOMED SYSTEM includes an originating exchange unit including circuitry configured to transmit, to a receiving exchange unit, a query request including predetermined query criteria, and receive, from the receiving exchange unit, patient metadata corresponding to a patient. The system also includes a receiving exchange unit including circuitry configured to aggregate protein-protein interaction data from a first service unit, wherein the aggregation includes determining corresponding data standards managed by the first service unit and receiving the protein-protein interaction data from the first service unit in the determined corresponding data standards. The receiving exchange unit can generate, in response to receiving the query request, the patient metadata corresponding to the patient, and transmit the patient metadata to the originating exchange unit.

23 Claims, 19 Drawing Sheets

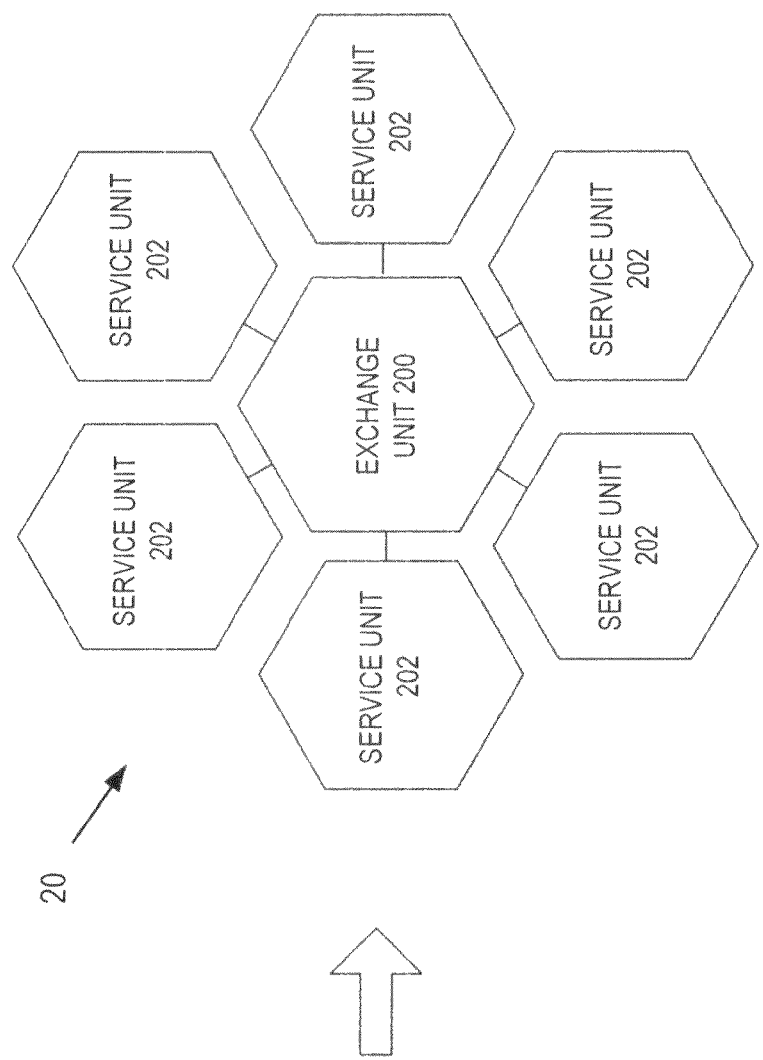
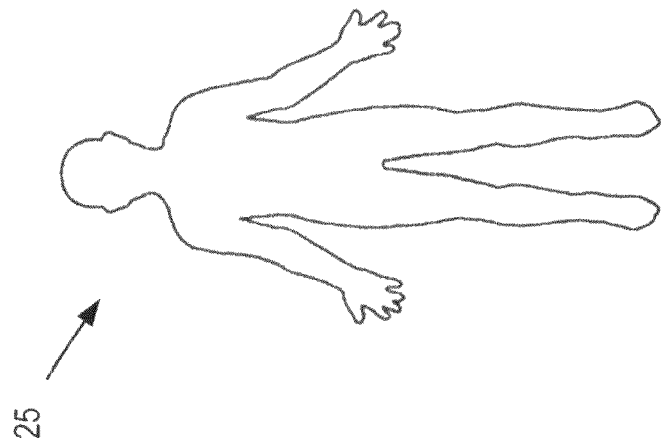
FIG. 2 get_Metatypic Data-Results ("

<Patient Encp_ID=1234567, Patient Encp_ID=7654321/>

Biographic Data, Diagnosis-Problems List, Medications List, Procedures, Surgical History, Treatment History, Allergy List, Vital Signs, Units of Measure, Key Findings, Laboratory Orders & Results, Micro-Pathology/Cytology, Radiology Images, Signals, Radiology Reports, Ambulatory Data Records, Progress Notes, Quality Measure, Operative Notes, Departmental Reports, Discharge Summaries, Gene Expression, DNA Sequence, Microarray Data, MiRNA Expression, Chromosomal Copy #, Loss of Hertrozygocity, Methylation Patterns, Nucleotide Sequence, Sequence Variation, Family Genetic Data, Eligibility, Concurrent Therapy, Assessment Test, Adverse Events, Gene Fusion, Phylogenetic Profiles, Ortholog Interaction, Domain Interaction, Microarray Gene Co-expression, Enzyme Records, Metabolic (Biological) Pathways, Non-Metabolic Pathways, Networks of Metabolic Pathways, Networks of Non-metabolic Pathways, Functional Hierarchies, Biological Processes, Genes, Drugs, Diseases, Interventions_Code=1234, 2345, 3456, etc./>

Use_Standard Code= HL7 Version 2,3, ADT, CCOW, EDI Exchange Formats, IEEE 1073, XDS, NCPD (X12N), MTOM, SAML, SOAP, UDDI, WS-Addressing, WSDL, WS-Security, XMI, XML Schemas")

*FIG. 11A* merge_Metatypic Data-Results ("

<Patient Encp_ID=0987654, Patient Encp_ID=3210987, Patient Encp_ID=3456789, etc />

Biographic Data, Diagnosis-Problems List, Medications List, Procedures, Surgical History, Treatment History, Allergy List, Vital Signs, Units of Measure, Key Findings, Laboratory Orders & Results, Micro-Pathology/Cytology, Radiology Images, Signals, Radiology Reports, Ambulatory Data Records, Progress Notes, Quality Measure, Operative Notes, Departmental Reports, Discharge Summaries, Gene Expression, DNA Sequence, Microarray Data, MiRNA Expression, Chromosomal Copy #, Loss of Hertrozygocity, Methylation Patterns, Nucleotide Sequence, Sequence Variation, Family Genetic Data, Eligibility, Concurrent Therapy, Assessment Test, Adverse Events, Gene Fusion, Phylogenetic Profiles, Ortholog Interaction, Domain Interaction, Microarray Gene Co-expression, Enzyme Records, Metabolic (Biological) Pathways, Non-Metabolic Pathways, Networks of Metabolic Pathways, Networks of Non-metabolic Pathways, Functional Hierarchies, Biological Processes, Genes, Drugs, Diseases, Interventions_Code=1132, 3340, 4455,6677, 8499, 0081, 3367etc./>

Use_Standard Code= HL7, ICD-9-CM/10, CCS, SNOMED CT, RxNorm, NDF-RT, NCPDP, CCR, CPT-4, SNOMED CT, UNII, CDA Template, UCUM, HL7 CDA Release 2, CCD, LONIC, CytometryML, DICOM, SACS, CMS PQRI, Genetic Variation: Informative, ANSI/HL7 V3 CGPED, R1-2007, MIAME, MAGE-ML , HL7 V3 CG GV, R1, HL7 V3 CG_GENO, R1-2007 (DSTU), XML schema ( GMD), OMIM, GO, SAM, ASN.1, GSVML, Pedigree: Normative, ANSI, CDISC, DRG, CPT-4, HCPCS, PSI-MI, MIAPE, BioPax, SBML, NDC, RxNorm, NDF-RT, NCPDP, ICD-9-CM/10, CCS")

*FIG. 11B*

SYSTEM AND METHOD FOR PERSONALIZED BIOMEDICAL INFORMATION RESEARCH ANALYTICS AND KNOWLEDGE DISCOVERY

This application was prepared with financial support from the Saudia Arabian Cultural Mission.

BACKGROUND

1. Technical Field

The present disclosure relates to the field of biomedical informatics. In particular, the present disclosure relates to a system and method for personalized biomedical information research analytics and knowledge discovery.

References

Aspects of this disclosure relate to the teachings of the following references, which are referred to throughout:

[1] Hagglund M, Scandurra I, Mostrom D, Koch S: Integration architecture of a mobile virtual health record for shared home care. *Stud Health Technol Inform* 2005, 116: 340-345.

[2] Hanss S, Schaaf T, Wetzel T, Hahn C, Schrader T, Tolxdorff T: Integration of decentralized clinical data in a data warehouse: a service-oriented design and realization. *Methods Inf Med* 2009, 48(5):414-418.

[3] Fayyad, U., Piatetsky-Shapiro, G., Smyth, P., and Uthurusamy, R., editors (1996). *Advances in Knowledge Discovery and Data Mining*. AAAI/MIT Press.

[4] Leach S M, Tipney H, Feng W, Baumgartner W A, Kasliwal P, Schuyler R P, Williams T, Spritz R A, Hunter L: Biomedical discovery acceleration, with applications to craniofacial development. *PLoS Comput Biol* 2009, 5(3): e1000215.

[5] Schonbach C, Kowalski-Saunders P, Brusic V: Data warehousing in molecular biology. *Brief Bioinform* 2000, 1(2): 190-198.

[6] Castellano M, Mastronardi G, Bellotti R, Tarricone G: A bioinformatics knowledge discovery in text application for grid computing. *BMC Bioinformatics* 2009, 10 Suppl 6:S23.

[7] Xiong J, Rayner S, Luo K, Li Y, Chen S: Genome wide prediction of protein function via a generic knowledge discovery approach based on evidence integration. *BMC Bioinformatics* 2006, 7:268.

[8] Viksna J, Celms E, Opmanis M, Podnieks K, Rucevskis P, Zarins A, Barrett A, Neogi S G, Krestyaninova M, McCarthy M I et al: PASSIM—an open source software system for managing information in biomedical studies. *BMC Bioinformatics* 2007, 8:52.

[9] Tsai Y S, King P H, Higgins M S, Pierce D, Patel N P: An expert-guided decision tree construction strategy: an application in knowledge discovery with medical databases. *Proc AMIA Annu Fall Symp* 1997:208-212.

[10] Weeber M, Klein H, Aronson A R, Mork J G, de Jong-van den Berg L T, Vos R: Text-based discovery in biomedicine: the architecture of the DAD-system. *Proc AMIA Symp* 2000:903-907.

[11] Friedrich C M, Dach H, Gattermayer T, Engelbrecht G, Benkner S, Hofmann-Apitius M: @neuLink: a service-oriented application for biomedical knowledge discovery. *Stud Health Technol Inform* 2008, 138:165-172.

[12] Parmee I C: Human-centric intelligent systems for exploration and knowledge discovery. *Analyst* 2005, 130 (1):29-34.

[13] Brandt C A, Deshpande A M, Lu C, Ananth G, Sun K, Gadagkar R, Morse R, Rodriguez C, Miller P L, Nadkarni P M: TrialDB: A web-based Clinical Study Data Management System. *AMIA Annu Symp Proc* 2003:794.

[14] Katehakis D G, Sfakianakis S G, Kavlentakis G, Anthoulakis D N, Tsiknakis M: Delivering a lifelong integrated electronic health record based on a service oriented architecture. *IEEE Trans Inf Technol Biomed* 2007, 11(6):639-650.

[15] Blobel B G, Engel K, Pharow P: Semantic interoperability—HL7 Version 3 compared to advanced architecture standards. *Methods Inf Med* 2006, 45(4):343-353.

[16] Brandt C A, Gadagkar R, Rodriguez C, Nadkarni P M: Managing complex change in clinical study metadata. *Journal of the American Medical Informatics Association: JAMIA* 2004, 11(5):380-391.

[17] Munro R E, Guo Y: Solutions for complex, multi data type and multi tool analysis: principles and applications of using workflow and pipelining methods. *Methods Mol Biol* 2009, 563:259-271.

[18] Wozak F, Ammenwerth E, Horbst A, Sogner P, Mair R, Schabetsberger T: IHE based interoperability—benefits and challenges. *Stud Health Technol Inform* 2008, 136: 771-776.

[19] Sarkar I N, Cantor M N, Gelman R, Hartel F, Lussier Y A: Linking biomedical language information and knowledge resources: GO and UMLS. *Pac Symp Biocomput* 2003:439-450.

[20] Bodenreider O: Biomedical ontologies in action: role in knowledge management, data integration and decision support. *Yearb Med Inform* 2008:67-79.

[21] U.S. Department of Health and Human Services. "Glossary of Terms for Personalized Health Care Website." 22 May 2013. <http://www.hhs.gov/myhealthcare/glossary/glossary.html>.

[22] Benner S A, Hoshika S, Sukeda M, Hutter D, Leal N, Yang Z, Chen F: Synthetic biology for improved personalized medicine. *Nucleic Acids Symp Ser (Oxf)* 2008(52): 243-244.

[23] Hoffman M A: The genome-enabled electronic medical record. *J Biomed Inform* 2007, 40(1):44-46.

[24] Rindfleisch T C, Brutlag D L: Directions for clinical research and genomic research into the next decade: implications for informatics. *J Am Med Inform Assoc* 1998, 5(5):404-411.

[25] Shah R, Dame B, Atar D, Abadie E, Adams K F, Zannad F: Pharmacogenomics in cardiovascular clinical trials. *Fundam Clin Pharmacol* 2004, 18(6):705-708.

[26] Scheuner M T, de Vries H, Kim B, Meili R C, Olmstead S H, Teleki S: Are electronic health records ready for genomic medicine? *Genet Med* 2009, 11(7):510-517.

[27] Brown S H, Lincoln M J, Groen P J, Kolodner R M: VistA—U.S. Department of Veterans Affairs national-scale HIS. *Int J Med Inform* 2003, 69(2-3):135-156.

[28] McGuire A L, Fisher R, Cusenza P, Hudson K, Rothstein M A, McGraw D, Matteson S, Glaser J, Henley D E: Confidentiality, privacy, and security of genetic and genomic test information in electronic health records: points to consider. *Genet Med* 2008, 10(7):495-499.

[29] Field D, Garrity G, Gray T, Morrison N, Selengut J, Sterk P, Tatusova T, Thomson N, Allen M J, Angiuoli S V et al: The minimum information about a genome sequence (MIGS) specification. *Nat Biotechnol* 2008, 26(5):541-547.

[30] Mailman M D, Feolo M, Jin Y, Kimura M, Tryka K, Bagoutdinov R, Hao L, Kiang A, Paschall J, Phan L et al: The NCBI dbGaP database of genotypes and phenotypes. *Nat Genet* 2007, 39(10):1181-1186.

[31] National Center for Biotechnology Information, U.S. National Library of Medicine. "dbGaP." 22 May 2013. <http://www.ncbi.nlm.nih.gov/gap>.
[32] National Institutes of Health. "Genetic Sequence Data Bank." 15 Jun. 2013. <http://www.ncbi.nlm.nih.gov/genbank/statistics>.
[33] Amanda C: Integration of Genomic and Phenotypic Data. In: *Data Analysis and Visualization in Genomics and Proteomics*. Edited by Francisco Azuaje J D; 2005: 83-97.
[34] El-Ghatta S B, Clade T, Snyder J C: Integrating Clinical Trial Imaging Data Resources Using Service-Oriented Architecture and Grid Computing. *Neuroinformatics*.
[35] Rademacher J D, Lippke S: Dynamic online surveys and experiments with the free open-source software dynQuest. *Behav Res Methods* 2007, 39(3):415-426.
[36] Fegan G W, Lang T A: Could an open-source clinical trial data-management system be what we have all been looking for? *PLoS Med* 2008, 5(3):e6.
[37] National Center for Biotechnology Information, U.S. National Library of Medicine. "EGFR epidermal growth factor receptor [*Homo sapiens* (human)].
[38] National Center for Biotechnology Information. "Activating mutations in the epidermal growth factor receptor underlying responsiveness of non-small-cell lung cancer to gefitinib." 20 May 2004. <http://www.ncbi.nlm.nih.gov/pubmed/15118073>.
[39] Couzin J: Pharmacogenomics. Cancer sharpshooters rely on DNA tests for a better aim. *Science* 2004, 305 (5688):1222-1223.
[40] Mirhaji P, Zhu M, Vagnoni M, Bernstam E V, Zhang J, Smith J W: Ontology driven integration platform for clinical and translational research. *BMC Bioinformatics* 2009, 10 Suppl 2:S2.
[41] Murphy S N, Mendis M, Hackett K, Kuttan R, Pan W, Phillips L C, Gainer V, Berkowicz D, Glaser J P, Kohane I et al: Architecture of the open-source clinical research chart from Informatics for Integrating Biology and the Bedside. *AMIA Annu Symp Proc* 2007:548-552.
[42] Murphy S N, Mendis M E, Berkowitz D A, Kohane I, Chueh H C: Integration of clinical and genetic data in the i2b2 architecture. *AMIA Annu Symp Proc* 2006:1040.
[43] Weber G M, Murphy S N, McMurry A J, Macfadden D, Nigrin D J, Churchill S, Kohane I S: The Shared Health Research Information Network (SHRINE): a prototype federated query tool for clinical data repositories. *J Am Med Inform Assoc* 2009, 16(5):624-630.
[44] Cesareni G, Ceol A, Gavrila C, Palazzi L M, Persico M, Schneider M V: Comparative interactomics. *FEBS Lett* 2005, 579(8):1828-1833.
[45] Dennis G, Jr., Sherman B T, Hosack D A, Yang J, Gao W, Lane H C, Lempicki R A: DAVID: Database for Annotation, Visualization, and Integrated Discovery. *Genome biology* 2003, 4(5):P3.
[46] Zhang J D, Wiemann S: KEGGgraph: a graph approach to KEGG PATHWAY in R and bioconductor. *Bioinformatics* 2009, 25(11):1470-1471.
[47] Cerami E G, Bader G D, Gross B E, Sander C: cPath: open source software for collecting, storing, and querying biological pathways. *BMC Bioinformatics* 2006, 7:497.
[48] Joshi-Tope G, Gillespie M, Vastrik I, D'Eustachio P, Schmidt E, de Bono B, Jassal B, Gopinath G R, Wu G R, Matthews L et al: Reactome: a knowledgebase of biological pathways. *Nucleic acids research* 2005, 33(Data base issue):D428-432.
[49] Cerami E G, Gross B E, Demir E, Rodchenkov I, Babur O, Anwar N, Schultz N, Bader G D, Sander C: Pathway Commons, a web resource for biological pathway data. *Nucleic acids research* 2011, 39(Database issue):D685-690.
[50] Siest G, Marteau J B, Visvikis-Siest S: Personalized therapy and pharmacogenomics: future perspective. *Pharmacogenomics* 2009, 10(6):927-930.
[51] Hewett M, Oliver D E, Rubin D L, Easton K L, Stuart J M, Altman R B, Klein T E: PharmGKB: the Pharmacogenetics Knowledge Base. *Nucleic Acids Res* 2002, 30(1): 163-165.
[52] Nadkarni, Prakash M., Randolph A. Miller. "Service-oriented Architecture in Medical Software: Promises and Perils." 22 May 2013. <http://jamia.bmj.com/content/14/2/244.extract>.
[53] International Business Machines. "Service Oriented Architecture." 22 May 2013. <http://www.ibm.com/soa>.
[54] Sun Microsystems. Java Technologies and Web Services Platforms White Paper. August 2005. 22 May 2013. <http://www.slgroup.com/Portals/O/docs/sample_docs/web_service_platform.pdf>.
[55] Research and Markets. "Services Oriented Architecture (SOA) Middleware Market Shares, Strategies, and Forecasts, Worldwide, 2013 to 2019." April 2013. 22 May 2013.
[56] Glaser J P: Too far ahead of the IT curve? *Harv Bus Rev* 2007, 85(7-8):29-33, 190; discussion 136-199.
[57] Kawamoto K, Honey A, Rubin K: The HL7-OMG Healthcare Services Specification Project: motivation, methodology, and deliverables for enabling a semantically interoperable service-oriented architecture for healthcare. *J Am Med Inform Assoc* 2009, 16(6):874-881.
[58] Daskalakis S, Mantas J: The impact of SOA for achieving healthcare interoperability. An empirical investigation based on a hypothetical adoption. *Methods Inf Med* 2009, 48(2):190-195.

2. Description of Related Art

Information complexity is a major problem in biomedical research. Data resources are fragmented and scattered either in heterogeneous systems or different repositories. The different data formats and multiple access methods, combined with poor integration, make data access by researchers cumbersome. Furthermore, the inability to cope with the newly generated biomedical metadata is equally important, in addition to the lack of ability to translate information into a meaningful knowledge for discovery.

The impact of continuing research practices in the current traditional way (and not having a solution) is disappointing. Neither researchers nor ordinary systems will be able to muddle through the mounting data (signals, sequences, imaging, etc.) that are generated every day from a single patient. Most of the existing architectures in biomedicine are neither service-oriented, nor data exchange enabled. The current services and models lack common standards and tools of data integration and exchange. The integration of data from various decentralized clinical parties in one data warehouse has been a major challenge for Service Oriented Architecture (SOA). Currently, mobile virtual patient health record systems are utilizing services of SOA integrative architecture [1]. However, careful requirements analysis of the data integration process will result in the desired design [2].

Therefore, it is important to design a system that enables users to conduct personalized research in the context of a health information research exchange with the end in mind. Therefore, the main goal should be facilitating discovery in medical care practices. Apparently, the impact of not having such solution is a slow knowledge discovery rate.

In brief, current research in healthcare is fragmented, non-personalized and does not utilize patient's data over time. The data sources are heterogonous and operated by non-interoperable systems. Consequently, this drives the cost of healthcare research up and the quality of the conducted research down.

Discoveries in biomedicine are still trivial given the amount of generated metadata (i.e., "big data") worldwide. Readiness is an issue in that the current biomedical knowledge mostly is not technology enabled for discovery. Knowledge discovery is defined as "the non-trivial process of identifying valid, novel, potentially useful, and ultimately understandable patterns in data" [3]. Available knowledge discovery applications in biomedicine are either solely literature-focused [4], or confined merely to biology [5], bioinformatics [6], genomics [7], and/or just for management [8]. Further, current systems are often outdated [9], trifling [10], non-scalable [7, 11], and/or not contextually-oriented [12]. Lack of proper research exchange architecture for knowledge discovery in biomedicine is resultant from jumping to data analysis before thoughtfully thinking about the complexity of the design and the dimensions of information management in such a multidisciplinary environment.

Commercial medical informatics software and systems still have limited functionality and persistent problems. The software and systems continue to have a high per-seat cost, proprietary architecture, limited built-in functionality, and limited or no support for binary data. In addition, current commercial software and systems are unable to be customized for special purposes futuristically [13].

Current systems also lack personalization—it is known that every patient is different. However, the practice of generalization of results from research conducted on a group of people who are thought to be similar in some conditions is not good enough. Research practices should be transformed from result-inferring practice into direct conjecture of the case itself based on personalization. Whenever personalized research is conducted on a patient, a more accurate judgment of the use preventive, diagnostic, and therapeutic interventions will be achieved. There is a need to develop research-oriented applications that are patient-centered (personalized) and use contextual analysis in data mining to enable researchers to be more efficient in knowledge discovery.

Additionally, there is a need for an integrated lifelong (longitudinal) medical record to access clinical data anytime in patient life [14]. Similarly, there is also a need to have a long-term personalized research application that is able to follow patient related data over time. In today's research we lack time layering research-based applications. Indeed, assuring that time trends (time-sensitive) are taken into consideration will add unprecedented value to the future of healthcare research and biomedical knowledge discovery.

Moreover, there is a need for a real-time research-based exchange. Often times, there is a new therapy that is discovered and surprisingly many patients do not know about it. Therefore, physicians and researchers should be informed about such discoveries in order to recommend them to their patients, thereby creating the need for a real-time information exchange for discovery.

SUMMARY

Among other things, the present disclosure is directed to a system and methods for simplifying the information complexity in biomedical and clinical research. In particular, the present disclosure describes aspects of a biomedical informatics research system that exchanges large datasets from disparate systems having varied data types.

Future biomedical research methods should not only focus on comparing a single patient with others based on their similarities (e.g., in signs, symptoms, lab results, and imaging), but should also consider contrasting patients based on their relevantly matching datasets. In order to achieve this, we must effectively be able to utilize information technology in biomedicine and design a system architecture to serve as a research enterprise system. The importance of conducting personalized research (through gathering research-based data from one individual) is to be able to integrate metadata from one patient with another patient (with a comparable condition) and generate a continuum of research-based driven knowledge. Moreover, future research-based information and communication technology in healthcare should be open, flexible, scalable, and knowledge-based. It should be research-oriented and built on data standard and information integrity [15].

Metadata in the areas of biomedical and clinical research in particular is becoming more complex due to lack of knowledge-based schema that centrally store and manage information about the various metadata. Therefore, maintaining such unstructured schemas remain real challenges especially in clinical trial research [16, 17]. The complexity is either due to semi-structured data, schema complexity, or unstructured content (e.g., external sources, Extensible Markup Language (XML), Resource Description Framework (RDF), SOA and Enterprise Service Bus (ESB)). This leads to major challenges for users, e.g., in figuring out what data is available and how to query it. Moreover, it creates challenges for systems as well such as unanticipated queries and complex query structures. Additional problems in existing systems include fragmentation of existing data resources, multiple repositories, heterogeneous environments, cumbersome data access and poor integration, multiple access methods, different schema, different data formats, high total costs, difficulties in scaling and making changes, under-utilized resources, and data security. Hence, the recipe for knowledge discovery in biomedicine is to provide flexibility of semi-structured data, to ease the use of search, and to provide better analytical tools. The science and technology of biomedical informatics should empower personalized medicine to solve these data problems.

Information integration is needed to connect related data (e.g., by target, pathway, etc.) and to provide unified access to data regardless of source. Information integration should enable platform data in context, provide all information required for decision support, and allow users to focus on research questions rather than data access (i.e., schemata, query languages, source location).

Therefore, new approaches should be used to overcome the lack of appropriate biomedical data aggregation, integration, and utilization. The present disclosure describes a new approach (hereinafter called a Health Information Virtual Exchange (HIVE) BIOMED SYSTEM) to help in solving this problem and to accelerate knowledge-driven discoveries for personalized biomedical research.

With meaningful research in mind, the HIVE BIOMED SYSTEM will differ from other existing developed systems by being comprehensive (i.e., most complete data about an individual patient), harboring trending patient metadata (i.e., longitudinal data) over time resembling continuous monitoring in a research context, and providing query-based research capabilities.

In one embodiment of the present disclosure, a HIVE biomedical information research analytics and knowledge discovery system includes an originating exchange unit including circuitry configured to transmit, to a receiving exchange unit, a query request including predetermined query criteria, and receive, from the receiving exchange unit, patient metadata corresponding to a patient. The HIVE biomedical information research analytics and knowledge discovery system also includes a receiving exchange unit including circuitry configured to aggregate protein-protein interaction data from a first service unit, wherein the aggregation includes determining corresponding data standards managed by the first service unit and receiving the protein-protein interaction data from the first service unit in the determined corresponding data standards. The receiving exchange unit can generate, in response to receiving the query request, the patient metadata corresponding to the patient, and transmit the patient metadata to the originating exchange unit.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 2 illustrates an exemplary personalized research hub according to one aspect of the present disclosure;

FIGS. 11A and 11B illustrate an exemplary process of performing data exchange from one metatypic core exchange unit with another metatypic core exchange unit in the personalized research network according to one aspect of the present disclosure;

DETAILED DESCRIPTION

Figure 1:
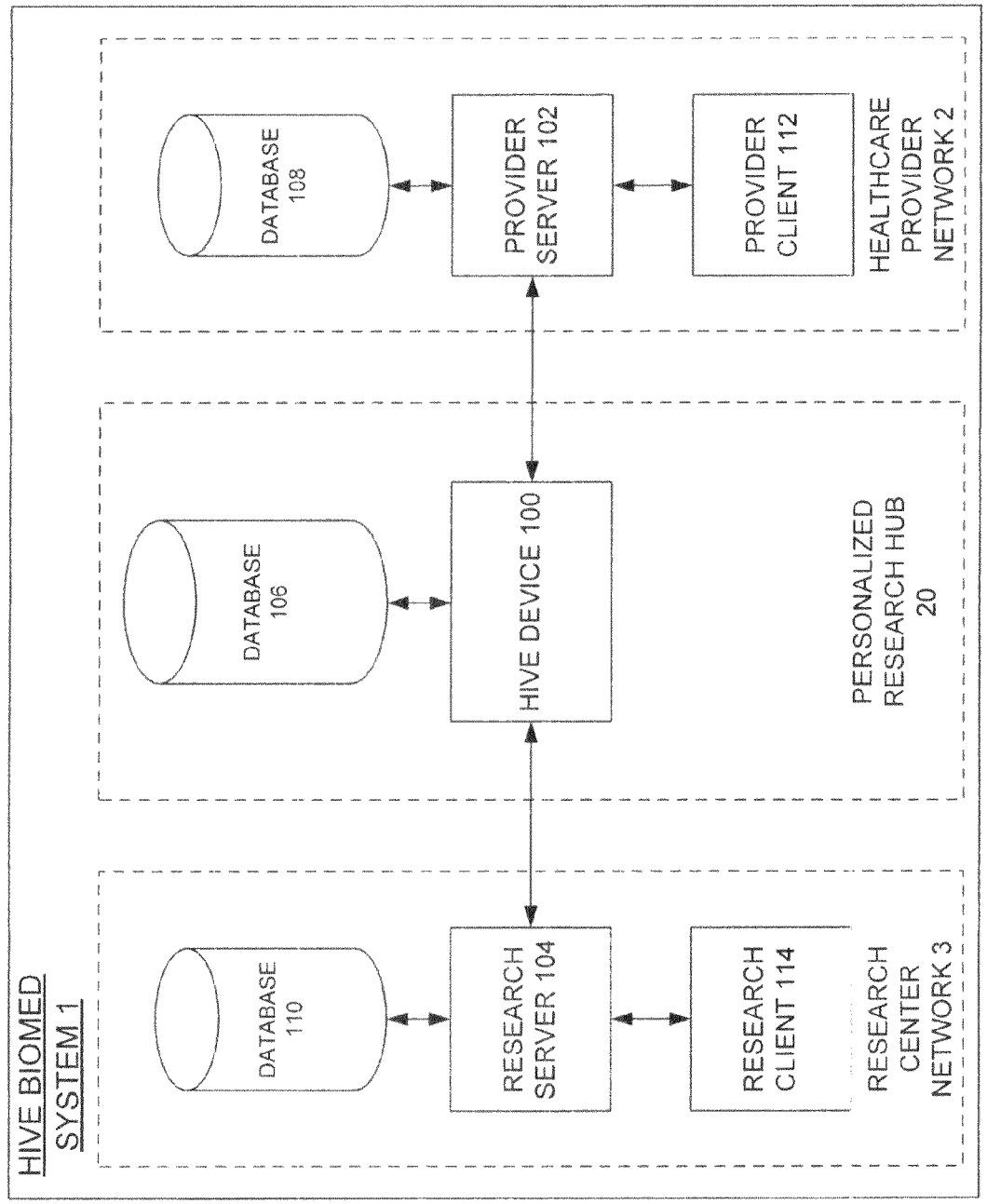
FIG. 1 illustrates an exemplary network overview of a HIVE BIOMED SYSTEM according to one aspect of the present disclosure.

Referring now to the drawings, wherein like reference numerals designate identical or corresponding parts throughout the several views.

FIG. 1 illustrates an exemplary network overview showing relationships between elements of a HIVE BIOMED SYSTEM 1 according to one aspect of the present disclosure. While not limiting, the HIVE BIOMED SYSTEM architectural framework described herein is preferably designed on the assumption that it will be suitable for a tertiary-care hospital that has a research center facility. It is also assumed that the hospital operates its medical records electronically. Further, its research center should preferably have significant biomedical research activities and sufficient data warehousing capability.

Referring to FIG. 1, the exemplary HIVE BIOMED SYSTEM 1 depicts a high-level design illustrating the relationship between a tertiary-care hospital (healthcare provider network 2) and a biomedical research center (research center network 3). A HIVE device 100 serves as a personalized research hub 20 (discussed in detail in later paragraphs) that will work as a midpoint system were both the hospital and the research center will be able to contribute to the HIVE BIOMED SYSTEM 1 and translate research outcome into tools (e.g. diagnostics) or treatments (e.g., therapies).

The exemplary HIVE BIOMED SYSTEM 1 includes the HIVE device 100 interfacing with a provider server 102 and a research server 104 via a network, such as the Internet, a WAN, a LAN, or the like. The HIVE device 100 also interfaces with a database 106, which may include a plurality of database memory arrays serving the various data types used in processing methods described herein. The provider server 102 and the research server 104 respectively interface with a database 108 and a database 110. In one aspect of the present disclosure the database 108 may include one or more database memory arrays for storing patient information (e.g., electronic medical records (EMRs)) collected by healthcare providers attached to the healthcare provider network 2, and the database 110 may include one or more database memory arrays for storing, e.g., disease registries, clinical trials data, and genomics data, which is collected by researchers included in the research center network 3. In certain aspects of the present disclosure, the research server 104 and/or the provider server 102 may correspond to a personalized research hub or a personalized research network of the research center network 3 and the healthcare provider network 2, respectively. The databases represented in FIG. 1 may have a similar structure.

A provider client 112 may be included in the HIVE BIOMED SYSTEM 1 as a user interface for healthcare providers in the healthcare provider network 2, and to transmit/receive data across the HIVE BIOMED SYSTEM 1. Similarly, a research client 114 may be provided as a user interface for researchers accessing the HIVE BIOMED SYSTEM 1 on the research center network 3. In certain embodiments, the HIVE device 100, the provider client 112, and/or the research client 114 may be configured to accept queries for data stored/managed by other elements connected via the network of the HIVE BIOMED SYSTEM 1. The skilled artisan will appreciate that while a single client device, server device, and database is illustrated in the respective networks of FIG. 1 for simplicity, this should not be construed as limiting, and aspects of the present disclosure may easily be adapted to accommodate a plurality of such devices connected in a network.

Health Information Exchange

Health Information Exchange (HIE) is the transmission of health-related standardized data across integrated systems in healthcare organizations.

As a rule of thumb, when proper standards are used based upon framework needs, usually the healthcare research infrastructure capabilities will reach new heights. The key elements of the health information exchange are data standards, data aggregation, metadata integration, and metadata exchange. Categorically, most common biomedical terminology standards are created for diagnoses, clinical symptoms, findings, drugs, laboratory, procedures, diagnostic studies, and medical devices.

Unfortunately, the upside of information sharing and data exchange is not obvious yet to many of the healthcare institutions. Only few hospitals that have EMR systems and conduct research can realize and appreciate the advantage of sharing information across organizations. An example is the Integrating the Healthcare Enterprises initiative (IHE) profiles, which has made a major contribution to optimized workflows and communication between different healthcare institutions [18].

The integration of diverse informatics terminologies is a fundamental prerequisite for the success of any biomedical research project supporting personalized medicine. There are a number of structured terminologies used in biomedicine that have been used extensively and have served as a unified coding scheme across information systems [19]. These include: (1) Systematized Nomenclature of Human Medicine (SNOMED); (2) Systematized Nomenclature of Medicine—Clinical Terms (SNOMED CT); (3) Logical Observations, Identifiers, Names and Codes (LOINC); (4) Minimum Information About a Microarray Experiment (MIAME); (5) Unified Medical Language System (UMLS); (6) Gene Ontology (GO); and (7) Online Mendelian Inheritance in Man (OMIM), a database that comprises codes for complex genetic diseases.

Data Exchange Standards

Three major data exchange standards include clinical trials data standards, clinical care data standards, and interoperability standards. The clinical trials data standards include Clinical Data Interchange Standards Consortium (CDISC) and Cancer Biomedical Informatics Grid (caBIG). Whereas, the clinical care data standards include Health Level Seven (HL7) versions 2 & 3, Reference Information Model (RIM) and Clinical Document Architecture (CDA). The interoperability standards include standards such as the Electronic Source Data Interchange (eSDI).

In brief, although standards and terminologies are not leveraged enough in healthcare but, there is considerable number of biomedical ontologies and standards that can enable data integration and healthcare research knowledge management [20]. Tools for meaningful biomedical knowledge analytics and discovery have yet to be invented.

Sources of Metadata

In certain aspects of the present disclosure, devices connected via a network on the HIVE BIOMED SYSTEM 1 serve as a personalized research hub(s) for aggregating metadata corresponding to one or more entities such as a patient. Aggregated metadata from the personalized research hubs may then be exchanged such that near-time access to a vast array of patient data may be obtained, analyzed, and stored.

For the purposes of the present disclosure, "metadata" is an aggregate of data in a variety of formats from disparate sources (i.e., it does not refer to data about data).

There are known sources for data in health care that could be aggregated and utilized in clinical research. Accurate data collection and Information Technology (IT) governance lead to increased readiness of any medical institution for research analytics and business intelligence. The main sources for patient-level research may correspond to metadata derived from medical records, genomics data, and clinical trials.

With scalability in mind, although there are a fair number of genotype-phenotype studies that have thoroughly explored the importance of their correlation, there are only very few studies that extend that effort to address collectively other correlative assays like protein-protein interactions, disease pathways, and therapeutics.

Integrated metadata derived from these services may additionally provide targeted care based, e.g., on the patient's specific genetic code in order to provide a tailored approach to treatment [21]. Regarding personalization, people make choices based on factors such as information, personality, and social context. Therefore, in order to make a better decision, longitudinal health data acquired from home devices (such as cardiac rhythms, blood pressure, blood sugar, etc.) should be considered. These practices use preventive, diagnostic, and therapeutic interventions that are based primarily on patient history information and genetic tests. Tools to sequence the genomes of individual patients are becoming more available, yet cost is still the principle obstacle behind the inability of connecting genetic information to diagnosis, prognosis, and treatment [22]. The goal of personalization of care is to improve health outcomes and the health care delivery system, as well as the quality of life of patients everywhere.

Typically, health information sources in health care are known; however, the ability of a medical institution to collect, organize, and utilize its own information contributes to the success of its research readiness and structured data analytics. In light of the above, the key data elements of personalization that best serve the scope of the present disclosure should be inclusive and centered on metadata derived from patient's medical records, personal genomic data, personal clinical trial data, protein-protein interaction data, disease pathways data, and therapeutic data.

Table 1 provides a summary of HIVE BIOMED SYSTEM data sources and data types used throughout the present disclosure.

TABLE 1

| Data Sources and Data Types | |
|---|---|
| Data Source | Data Type |
| Patient Medical Record | Phenotypic Data |
| Genomic Record | Genotypic Data |
| Clinical Trials | Trialotypic Data |
| Protein-protein Interaction | Proteotypic Data |
| Disease Pathways | Pathotypic Data |
| Therapeutics | Theratypic Data |

A detailed description of the data sources and data types listed in Table 1, as well as exemplary sources for said data, will now be described.

Patient Medical Record

Advances in genetic information systems are mandated by the everyday generation of genetic data from patients. Linking the genotypic data with the phenotypic data into a genomic-based EMR will definitely facilitate the practice of clinical genomics. Basically, it will enhance the quantitative and qualitative methods used in the medical care setting and provide the best available medical care to patients. Researchers of bioinformatics and clinical informatics have incorporated clinical bioinformatics to improve health care, using biological and medical information Innovative genome-enabled EMRs will create opportunities to utilize such integral information in clinical decision, including computerized responses to personalized pharmacogenomics risks [23].

Modern healthcare practice is in need of more objective information on which to base healthcare decisions, and the accelerating progress and clinical impact of genomics research offers an important source of such information. The convergence of clinical medicine and the life sciences will result in new opportunities in clinical trials and clinically linked medical research [24]. Genomics medicine should include the use of an advanced EMR system implemented in a research-networking oriented model. Physicians are required to understand the concept of genetic variability, its interactions with the environment, and its implication for patient care. Treating patients through their genetics profiling and prescribing tailored pharmacogenomics medication will form the shape of our future personalized medicine [25].

Numerous open-source EMR systems are currently available for public. Meaningful EMR have the potential to enable clinical integration of genomic medicine and improve personalized healthcare delivery. However, structured and standardized data elements and advanced requirements are needed [26].

The "WorldVistA", a VistA software application, released through the Freedom of Information Act (FOIA) is a good example of an advanced clinical information system. It is open-source, reasonably economic, and certified by the CCHIT [27]. The confidentiality, privacy, and security of genetic and genomic information in EMR systems remain an issue. However, implementation of strict policies can facilitate the biological and clinical data resource development for research purposes [28].

Re-engineering of existing EMRs to include the genomic data integration has started to happen. This development will lead to a demand on further integration of the health care system for genomics medicine to produce better outcomes. The augmentation of Health Level Seven (HL7) International, a health care messaging standard, has also facilitated the introduction of genetic data into the EMR. Health information technology will change the way we look at biomedical research in the very near future.

Genotypic Data

The Genomic Standards Consortium (GSC) provided a report on the development of the Minimum Information about a Genome Sequence (MIGS) specification and the integrated Minimum Information about a Metagenome Sequence (MIMS) specification. The GSC has also indicated insights about restructuring the MIGS/MIMS XML schema [29]. There are a couple of genome database sources worldwide that hold personalized metadata. A good example is the National Center for Biotechnology Information (NCBI) database of Genotypes and Phenotypes (dbGaP). The dbGaP database was developed to investigate the association between genotypic data and individual-level phenotypic data [30].

Phenotypes & Genotypes

In 1909, Danish botanist Wilhelm Johannsen coined the word gene (using the Greek for "to give birth to"). The terms "genotype" and "phenotype" were created by him in 1911. Genotype refers to the genes an individual has, and phenotype is how those genes are expressed. While genotypic data may determine the presence or absence of a specific disease, phenotypic data is manifested by the gene expression or the manifestations of that specific disease. According to the "central dogma" of molecular biology, DNA is transcribed into RNA then translated to proteins, which then make small molecules. These proteins then manifested to create the outside characteristics of living creatures.

A phenotype is the apparent physical manifestation of a human such as eye or hair colors. A genotype is the inheritable information. PharmGKB defines genotype data as data regarding genomic variants such as Single Nucleotide Polymorphisms (SNPs), insertions and deletions [31]. For instance, DNA sequences, SNPs, transcriptomes, and proteomes are all examples of genotypic information. Phenotypic variations occur as a result of the discrepancy in the DNA sequence. Genotype can evidently be affected by environmental factors to get altered into a different phenotype; this phenomenon is called "phenotypic plasticity." The ability of an organism with a given genotype to change its phenotype is an important topic in the genotype-phenotype correlation. Environmental factors also play an important role in the development of a specific genotype to phenotype expression.

In biomedical sciences, a phenotype is defined simply as the outside physical manifestations which result from the gene inherited from the parents. Linking both phenotype and genotype at individual-level is a key step for the present disclosure. Phenotypic data are represented in various ways; either in simple textual format as in Online Mendelian Inheritance in Man (OMIM), in a complex quantitative format (text and values), or combinations of both formats. Thus, understanding the nature of complexity of the phenotypic representation is important to developing the database system requirement. Exploration of the association between specific genes and observable traits can be crucial in enhancing our understanding of diseases and for developing novel diagnostic methods and treatment.

According to the Genetic Sequence Data Bank at the National Center for Biotechnology Information (NCBI), it is estimated that there are over 150 billion Base Pairs of DNA and 162 Million Sequences in year 2013 [32]. This exponential growth represents the outstanding collaboration between biologists that should motivate clinicians as well to collaborate in translational research. Unfortunately, phenotypic data is conceivably the least analyzed. Thus, biomedical informatics, as a liaison between the two parties, should promote and support the creation of new technologies to integrate the phenotypic data with the genomic data. This will provide more opportunities for a genome-scale phenotype-genotype correlation [33].

Clinical Trials

Recently, SOA has been used to integrate clinical trial imaging data resources through middleware modular interoperability. Better control of de-identification of patients was achieved using the appropriate standards and tools [34]. A good example is dynQuest, which is an open-source Web-based trials software that manages dynamic questionnaire-based trials over the Internet as randomized control trials [35].

Likewise, one of the software involved in CaBIG is the OpenClinica, which is a free, open source clinical trials data-management system. The OpenClinica software is designed to support all types of clinical studies in multidisciplinary research settings and remains the most promising [36].

Translational Research

The strength of biomedical informatics is in the application of bioinformatics tools at the bench side delivering clinical results to the bedside and translating these innovative results into clinical practice. Thus, translational research is a unique integration of basic and applied sciences creating a continuum of medical discoveries that help in advancing clinical knowledge. As a result, translational research could innovatively improve medical care practices.

Presently, scientists are trying to speed up the feedback from the clinical informatics side (innovation in practice) to the bioinformatics side (bench) for further research and discovery. Biomedical informatics can effectively accelerate the cycle of translational clinical bioinformatics research. The National Institutes of Health (NIH) has created an initiative for promoting the concept of translational biomedical research. It is believed that such initiative will improve the interaction between basic and clinical investigators, which will improve the lives of patients affected with complex diseases like cancer.

A good example is the study conducted at the Massachusetts General Hospital related to activating mutation in the Epidermal Growth Factor Receptor (EGFR) in correlation with the lung cancer to Gefitinib therapy [37, 38]. Similarly, another study was conducted by Dana-Faber Cancer Institute. Both studies managed to merge molecular data with clinical data, resulting in translation into clinical practice, which has only taken 90 days to be a standard test used to help patients [39]. Thus, the ability to quickly translate discoveries from the bench into clinical orderable test is highly needed.

In ontology driven integrative platform, SOA is used to modularize and distribute reusable services in a dynamic and distributed environment [40]. A good example of clinical and translational research is the Informatics for Integrating Biology and the Bedside (i2b2), which is an interoperable framework for clinical research [41]. The "i2b2" was developed to enable investigators to collect and manage projects that integrate clinical and genetic data [42]. To serve the enterprise, the i2b2 was recently enhanced to include federated query tool for clinical data repositories. The project is called the Shared Health Research Information Network (SHRINE), which enables users to share data for research purposes across organizations [43].

Protein-Protein Interaction

Proteomics is the computational study of proteins' structures and functions. Unlike the static genome, the proteome changes constantly in response to different cellular signals. The proteome structure varies with health or disease and effects of drug treatments. Protein-Protein Interaction (PPI) is defined as the physical association of two or more protein molecules. Computationally, data about PPI comes from the interactome by using gene fusion, phylogenetic profiles, ortholog interaction, or microarray gene co-expression. PPI interactions are collected together in specialized biological databases that allow interactions to be assembled and studied further.

The significance of protein interaction is that distortions of protein interactions can cause diseases. Thus, PPI assay analysis can identify a new therapeutic approach. Through interactomics, comparative interactome can show smaller higher-confidence datasets with larger fraction of interactions [44].

Disease Pathways

Analysis of high-throughput data in the context of pathways provides insights about risk factors for complex human diseases. Moreover, visualization of pathways is mandated by the complexity of disease-drug mapping [45]. Thus, annotated gene-disease causal associations can be examined using disease pathway analysis.

Disease pathways data is important for phenotype-based drug discovery. For example, many of the neurodegenerative diseases such as Parkinson's disease have misfolding and aggregation of a specific protein. Pathway assay can identify disease-modifying agents for the treatment of Parkinson's disease. Currently, somatic mutations of known cancer diseases (e.g. colorectal cancer, pancreatic cancer, prostate cancer and acute myeloid leukemia, etc.) can be evaluated using pathway analysis [46].

There are a number of good open-source software systems for collecting, storing, and querying biological pathways such as cPath [47] and Reactome [48]. There are also authentic Web resources such as "Pathway Commons" for biological pathway where large data sets can be downloaded for analysis purposes [49].

Biological Databases

Based on literature review, it is estimated that there are currently over 850 biomedical databases worldwide. These databases are grouped into divisions based on their defined focus. These databases vary in their quality and perspectives. It has yet to be determined how many of these databases deal with the integration of phenotypic and genotypic data. The Gene Ontology (GO) provides a controlled vocabulary describing gene and gene product attributes in any organism.

Personalized Therapeutics

Personalized therapy is mandated by innovations in pharmacogenomics and drug development. Personalized therapy is becoming more possible through the power of genome-wide association studies that surpluses case-control studies [50]. Understanding the effects of individual genetic variants using pharmacogenetics and pharmacogenomics knowledge is readily available through "PharmGKB"; the Stanford Pharmacogenetics Knowledge Base. The PharmGKB is a repository of data to track associations between genes and drugs for pharmacogenomics discovery [51].

Conceptual Model of Personalized Research Hub

Next, FIG. 2 illustrates an exemplary conceptual model of a personalized research hub according to one aspect of the present disclosure. The personalized research hub of FIG. 2 may, e.g., correspond to the HIVE device 100 or any element/device sharing a network connection with the HIVE device 100 and/or the HIVE BIOMED SYSTEM 1.

Referring to FIG. 2, the exemplary conceptual model of personalized research hub 20 includes an exchange unit 200 and a plurality of service units 202. In general, each service unit 202 may contain one or more specific datasets related to the function of the unit. In certain aspects of the present disclosure, the one or more specific data sets of the service units 202 correspond to the source for metadata relating, e.g., to one or more patients. The exemplary model of FIG. 2 illustrates six service units; however, it should be appreciated that more or fewer service units may be included within the scope of the present disclosure.

Figure 3:
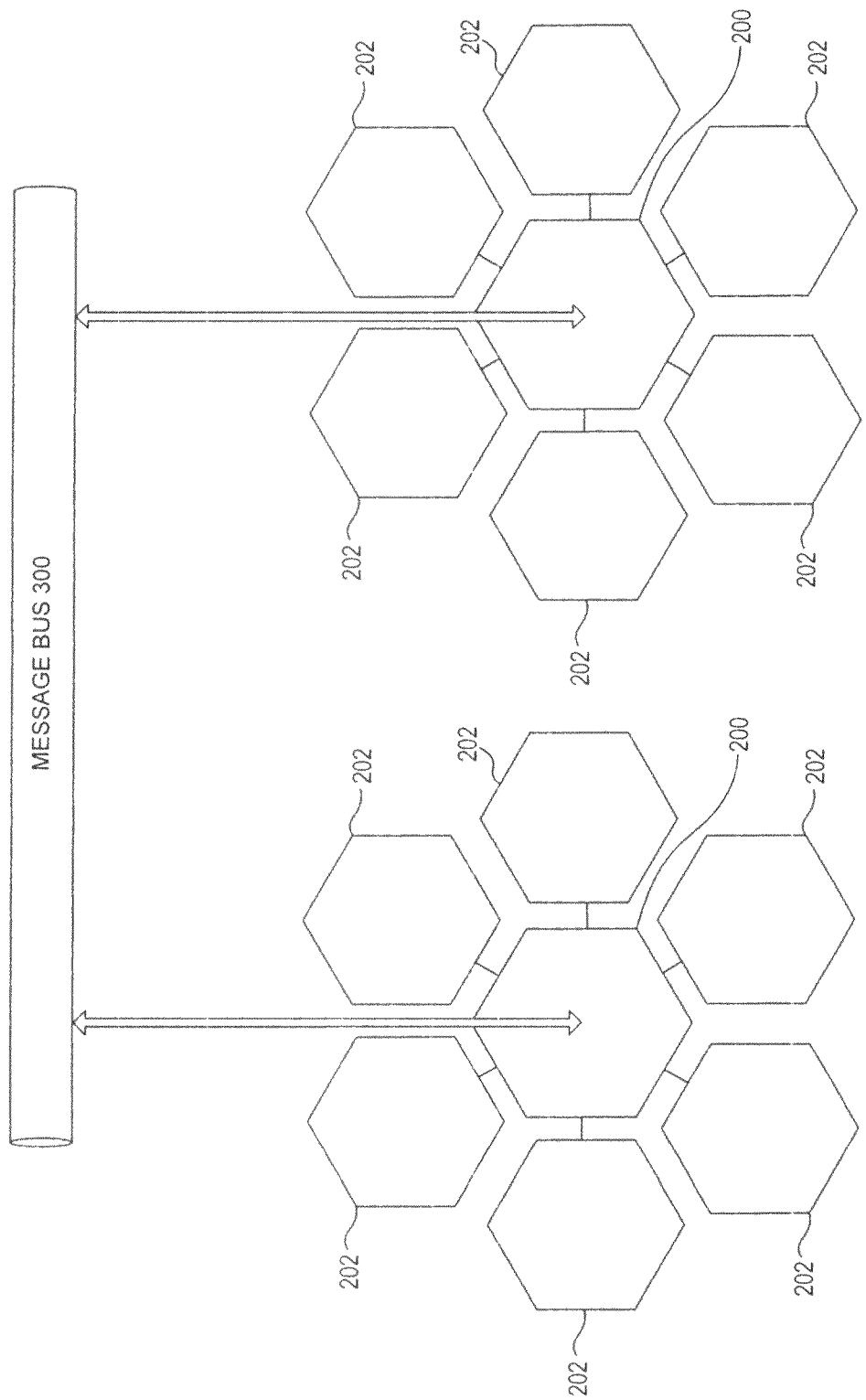
FIG. 3 illustrates a non-limiting example of personalized research hub data exchange according to one aspect of the present disclosure.

Each service unit 202 should be able to communicate with its respective core exchange unit 200 (communication between personalized research hubs via the exchange unit 200 is discussed later in relation to FIG. 3). The exchange unit 200 should be able to recognize different data types (i.e., metadata) and exchange relevant data with other exchange units in a network as needed. That is, in one aspect of the present disclosure, a plurality of personalized research hubs 20 may be connected via each hub's exchange unit 200. The exchange unit 200 should also be able to update one or more service units with new data that is recently exchanged (i.e., bi-directional data flow). Updates should preferably occur in real-time as patient data changes (e.g., new treatments received), and the updated data should be stored such that time-oriented analysis may be performed.

It should be appreciated that the personalized research hub corresponds to a single patient for the purposes of this disclosure, as illustrated by patient 25 in FIG. 2.

In one aspect of the present disclosure, the conceptual model illustrated in FIG. 2 may operate in accordance with a point-to-core-to-bus connectivity model. FIG. 3 illustrates a non-limiting example of personalized research hub communication in a point-to-core-to-bus connectivity model. Each exchange unit 200 of the point-to-core-to-bus model exchanges metadata with another exchange unit though a message bus 300. In certain embodiments, the exchange unit 200 may correspond to one patient, in which case each exchange unit 200 is able to exchange metadata sets with other exchange units corresponding to different patients in what is hereinafter referred to as a personalized research hub. It is noted that while the point-to-core-to-bus connectivity model is the preferred data exchange model, the skilled artisan will appreciate that aspects of the present disclosure may be adapted for other data exchange models such as point-to-point. Further, while only two personalized research hubs are illustrated in FIG. 3, the skilled artisan will appreciate that any number of hubs may be interconnected according to the principles of the present disclosure.

Conceptual Model of Personalized Research Network

Figure 4:
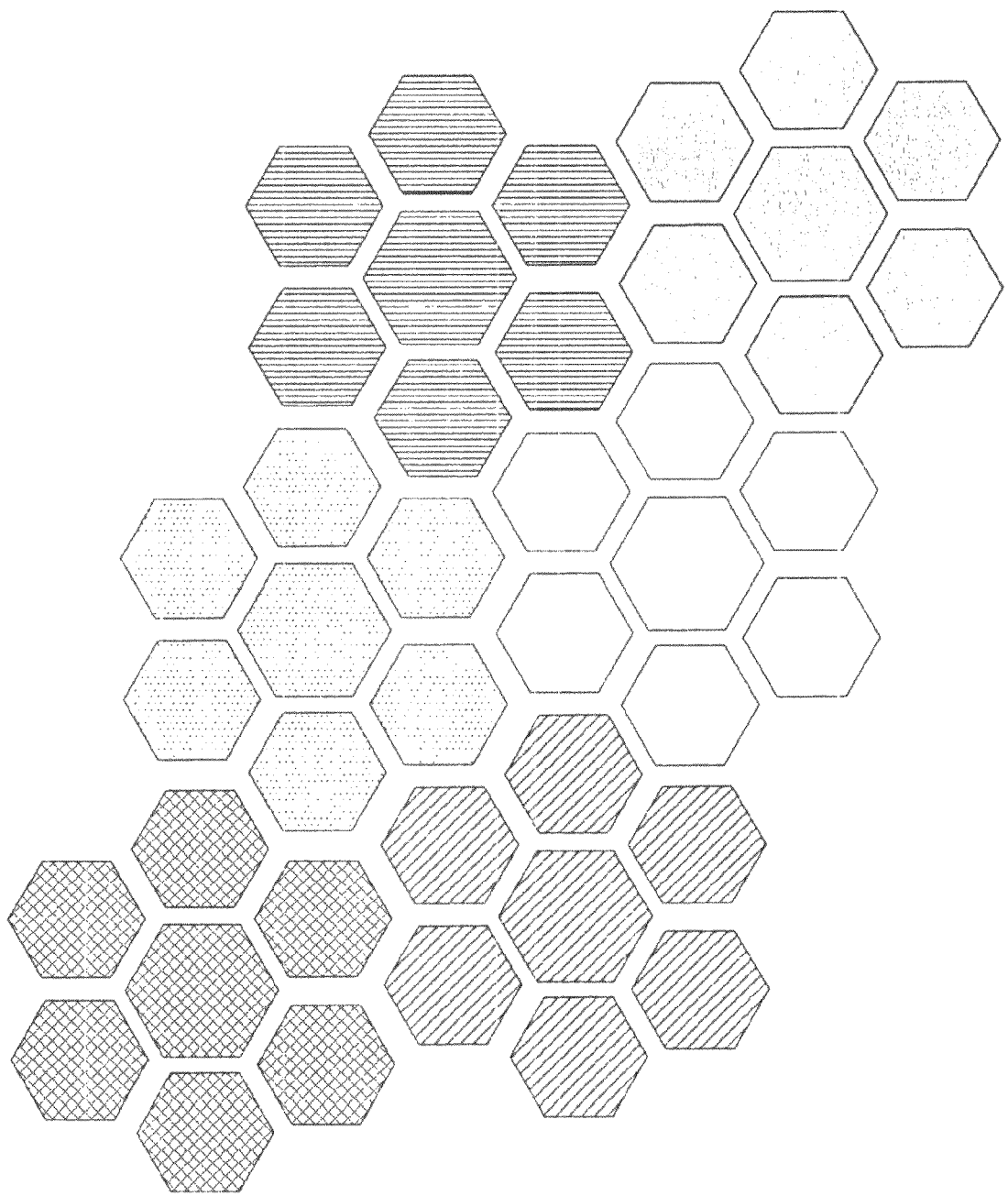
FIG. 4 illustrates an exemplary personalized research network model according to one aspect of the present disclosure.

Next, FIG. 4 illustrates an exemplary model corresponding to a network of personalized research hubs (i.e., a personalized research network). The exemplary model of FIG. 4 builds upon the concepts discussed above with respect to data exchange between exchange units. Six personalized research hubs similar that that of FIG. 2 (i.e., six research units and one exchange unit) are illustrated in the personalized research network model 400 of FIG. 4. Varied shading patterns distinguish the respective personalized research hubs in the figure. It should be appreciated that any number of personalized research hubs may form a personalized research network such as that shown in FIG. 4.

In one aspect of the present disclosure, aggregation, integration, and exchange of data corresponding to group of communal patients is the eventual goal of the personalized research network. FIG. 4 shows how a school of service units may work collectively to exchange meaningful data for research-based data mining and business intelligence. The service (research) units act as data resources that contain pre-identified datasets, while the exchange unit acts as a core hub for the individualized (patient-level) personalized research hub. The core exchange unit is responsible for metadata aggregation and exchange. In one embodiment, data aggregation and exchange is performed via a bus such as in the model shown in FIG. 3.

In certain aspects of the present disclosure, the personalized research network model 400 of FIG. 4 is a system in which data are physically stored and/or managed (and integrated) by each service and/or exchange unit included in the network. The respective service units may accept local and federated queries distributed through network. Queries may be run against the data stored and/or managed by the service units, and aggregated results may be returned to the end-user.

Figure 5:
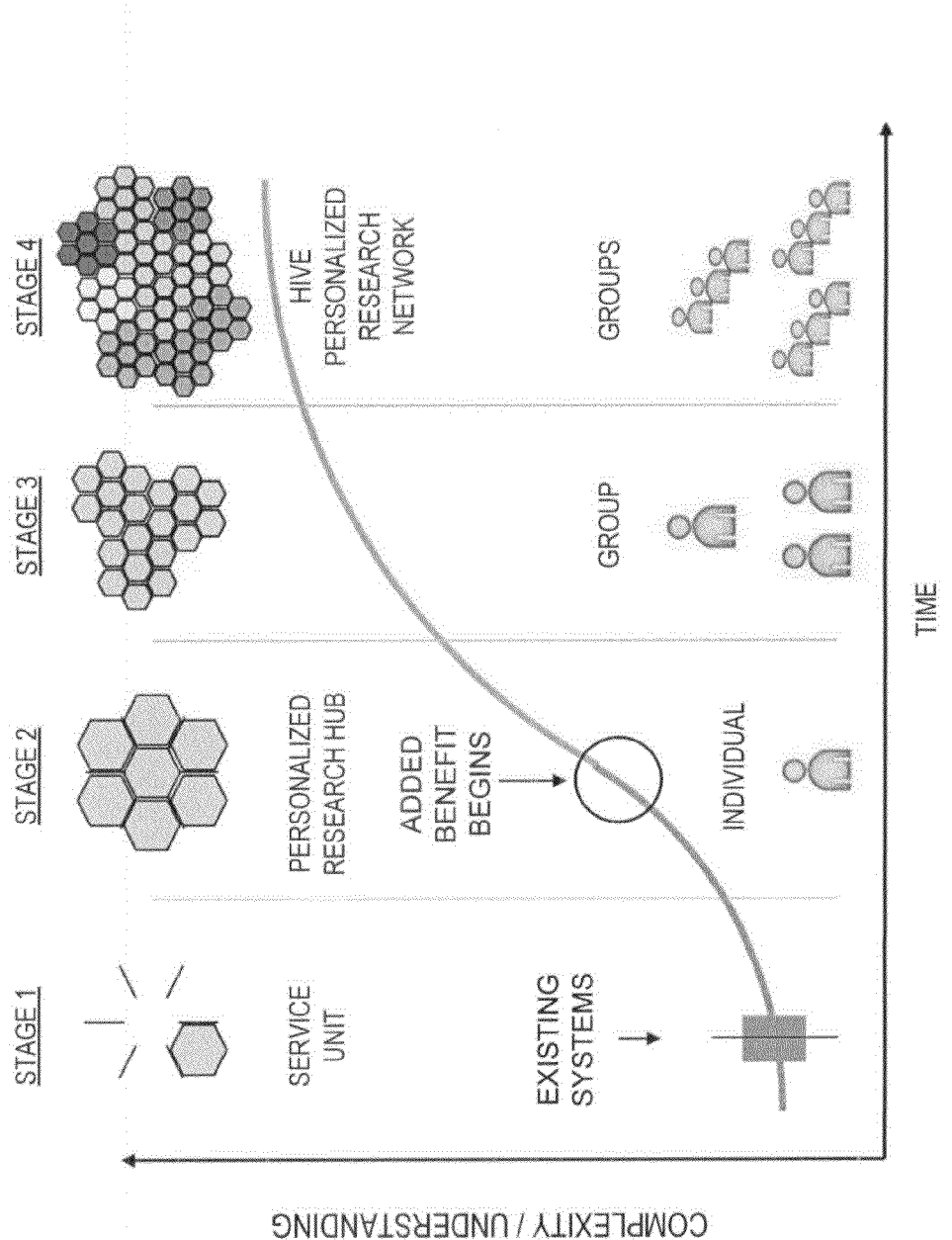
FIG. 5 shows an exemplary illustrated overview of various HIVE BIOMED SYSTEM units, their corresponding units in the context of a medical treatment and research environment, and a graphical representation of the benefits derived from such a structure.

Next, as a summary of the concepts and principles discussed thus far, FIG. 5 shows an illustrated overview of the various units in the above-described models, their corresponding units in the context of a personalized therapy and research environment, and a graphical representation of the benefits derived from such a structure. Referring to FIG. 5, the figure illustrates an evolution in system architecture and the corresponding growth in both complexity and understanding of data over time. The first stage is represented as a single service unit, which may correspond to data relating to a particular research-based source and/or another data type. It should be appreciated that the first stage represents the status quo of existing biomedical research systems. That is, current systems focus on a single individual, typically with a singular focus area, which is represented as a single service unit in the figure. Benefits added by aspects of the HIVE BIOMED SYSTEM begin in the second stage. The second stage is represented as a personalized research hub, which is formed by linking a plurality of service units with an exchange unit. In this example, the data managed by and/or stored in the service units corresponds to a single individual. By linking personalized research hubs via networking between exchanged units, personalized research networks may be formed corresponding to a group of individuals, as shown in the third stage. Shading variations represent individual personalized research hubs for each group member in the network. The links amongst the individuals in the group may, in certain aspects of the present disclosure, be determined based on commonalities between the individuals analyzed using a predetermined function that receives service unit data as an input. Further benefits in understanding may be realized in expanding the HIVE personalized research network such that groups of individual groupings are linked, as shown in stage four. The skilled artisan will appreciate that the benefits of the HIVE BIOMED SYSTEM vastly improve as the network expands since new hubs and/or networks increase the underutilized resources that the system may draw from to provide aggregated healthcare data.

FIG. 5 also depicts the importance of the longitudinal (time-oriented) architecture in conducting research. The arrow pointed to the circle on the graph corresponds to the point at which traditional research is transformed into a result-oriented longitudinal research through the HIVE BIOMED SYSTEM. That is, aggregating and exchanging data amongst groups of patients and more preferably groups of patient groupings provides a compounding benefit over time not realized by compartmentalized research and/or treatment. As shown in the graph, complexity of information will increase over time but our understating of complicated diseases and disorders will also increase by leveraging aspects of the present disclosure. Further, as more patients (or groups of patients) are added into this system selectively, comparability analysis and ultimately query results will improve, thereby leading to advanced longitudinal research analytics and knowledge discovery.

Exemplary Hive Biomed System Personalized Research Hub

Figure 6:
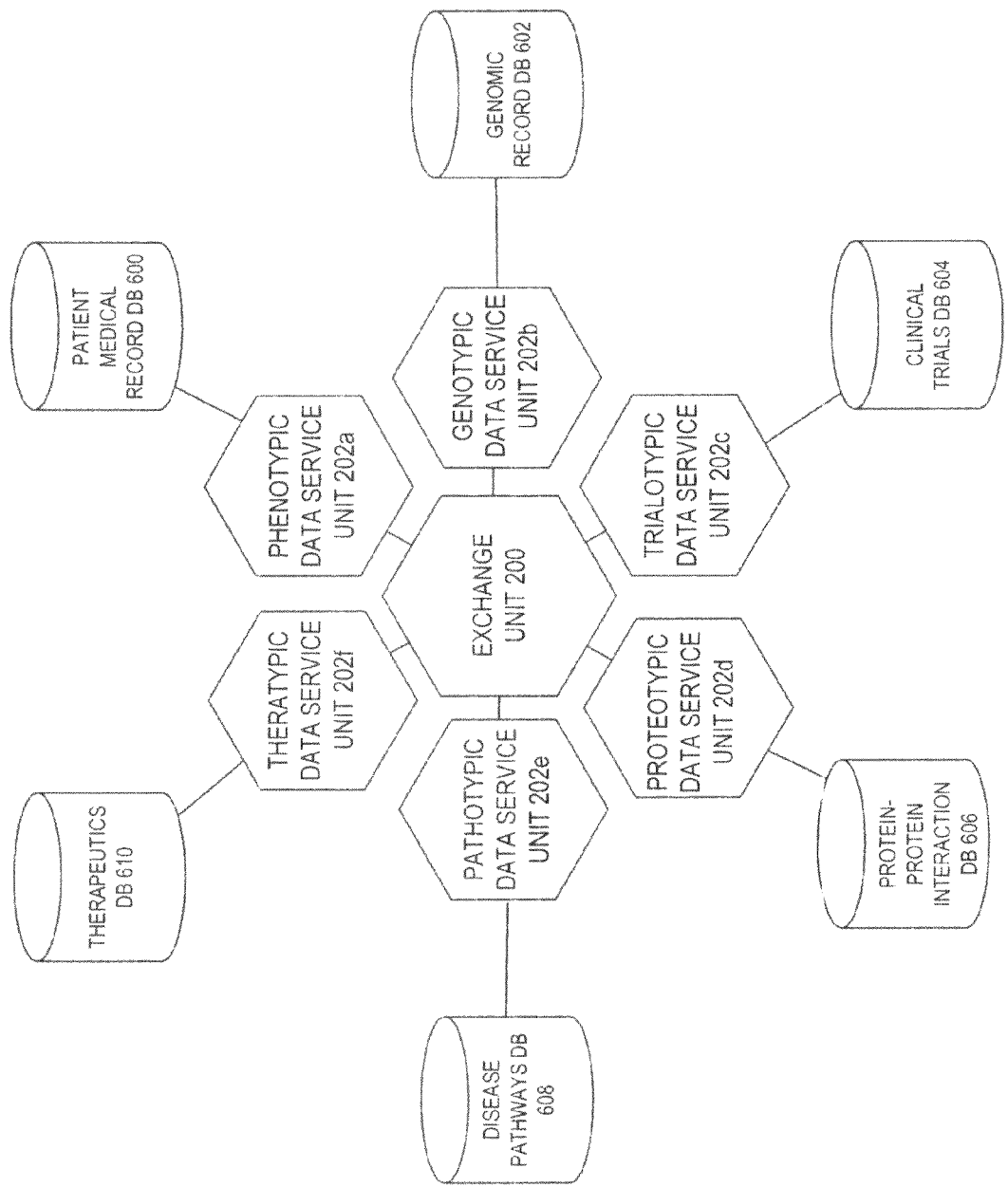
FIG. 6 illustrates a non-limiting example in which the conceptual model of FIG. 2 to specific exemplary data types exchanged in the HIVE BIOMED SYSTEM according to one aspect of the present disclosure.

Next, FIG. 6 illustrates a non-limiting example in which the conceptual model of FIG. 2 is adapted according to specific data types exchanged in the HIVE BIOMED SYSTEM 1. In particular, the exemplary configuration of FIG. 6 shows six service units 202 interfacing with data repositories corresponding to the data types described above with respect to Table 1.

Beginning with the phenotypic data service unit 202a and progressing clockwise around the exchange unit 200, the phenotypic data service unit 202a stores/manages data derived, e.g., from the patient electronic medical record. In this example, the phenotypic data service unit 202a interfaces with a patient medical record database (DB) 600, which may include one or more memory arrays configured to store the data stored/managed by this service unit. The genotypic data service unit 202b stores/manages data derived, e.g., from a patient's personal genomic record or from corresponding genomic data warehouses. In this example, the genotypic data service unit 202b interfaces with a genomic record database (DB) 602, which may include one or more memory arrays configured to store the data stored/managed by this service unit. The trialotypic data service unit 202c stores/manages data derived, e.g., from a patient's clinical trial record or from corresponding clinical trials data warehouses. In this example, the trialotypic data service unit 202c interfaces with a clinical trials database (DB) 604, which may include one or more memory arrays configured to store the data stored/managed by this service unit. The proteotypic data service unit 202d stores/manages data derived, e.g., from interactome data warehouses. In this example, the proteotypic data service unit 202d interfaces with a protein-protein interaction database (DB) 606, which may include one or more memory arrays configured to store the data stored/managed by this service unit. The pathotypic data service unit 202e stores/manages data derived, e.g., from pathways data warehouses. In this example, the pathotypic data service unit 202e interfaces with a disease pathways database (DB) 608, which may include one or more memory arrays configured to store the data stored/managed by this service unit. Lastly, the theratypic data service unit 202f stores/manages data derived, e.g., from pharmacogenomics data warehouses. In this example, the theratypic data service unit 202f interfaces with a therapeutics database (DB) 610, which may include one or more memory arrays configured to store the data stored/managed by this service unit.

Service units 202a-f in this example are assumed to be of a similar structure to the generic service unit 202 discussed above for FIG. 2.

Data Standards

There are known standards and terminologies corresponding to each of the research service units 202a-f; however existing systems fail to integrate metadata from disparate systems using the varied data standards. The present disclosure identifies the key data standards that will be considered by the HIVE BIOMED SYSTEM 1, then leverages these standards in order for the service units 202a-f to communicate collectively with their exchange unit 202, which by extension results in meaningful research networks being formed by interconnected exchange units 200 exchanging the derived metadata. Details about the standards corresponding to the service units and the exchange unit according to certain aspects of the present disclosure are described in detail below.

The following tables summarize the Minimum Data Requirements (MDRs) and their associated data standards for each of the six research service units 202a-f. The minimum data to be exchanged in the exemplary architectural data model are required for establishing maximum research analysis limits. Note from the tables that there are numerous competing standards that might independently address the same data element. Notably, some data standards are being used for more than one data element. For example, overlapping standards can be easily noticed in messaging (HL7), documents (CCR & CDA), and terminology (SNOMED, LONIC, ICD-9, RxNorm). Indeed, overlapping of standards is considered to be an added value for standards optimization. Further, note that the standards listed are non-limiting and other standards may be used within the scope of the present disclosure.

TABLE 2

Data and Standards - Phenotypic Data Service Unit

| Data Type | Content Exchanged | Key Standards |
| --- | --- | --- |
| Phenotypic Data | Biographic Data | HL7 |
| | Diagnosis-Problems List | ICD-9-CM/10, CCS, SNOMED CT |
| | Medications List | RxNorm, NDF-RT, NCPDP, CCR |

TABLE 2-continued

Data and Standards - Phenotypic Data Service Unit

| Data Type | Content Exchanged | Key Standards |
| --- | --- | --- |
| | Procedures | CPT-4, SNOMED CT |
| | Surgical History | SNOMED CT |
| | Treatment History | SNOMED CT |
| | Allergy List | UNII, CCR |
| | Vital Signs | CDA Template |
| | Units of Measure | UCUM |
| | Key Findings | HL7 CDA Release 2, CCD |
| | Laboratory Orders & Results | LONIC |
| | Micro-Pathology/Cytology | CytometryML |
| | Radiology Images | DICOM |
| | Signals | SACS |
| | Radiology Reports | CDA Template |
| | Ambulatory Data Records | HL7 CDA Release 2, CCD |
| | Progress Notes | CDA Template |
| | Quality Measure | CMS PQRI |
| | Operative Notes | HL7 CDA Release 2, CCD |
| | Departmental Reports | HL7 CDA Release 2, CCD |
| | Discharge Summaries | HL7 CDA Release 2, CCD |

TABLE 3

Data and Standards - Genotypic Data Service Unit

| Data Type | Content Exchanged | Key Standards |
| --- | --- | --- |
| Genotypic Data | Biographic Data | HL7 |
| | Gene Expression | Genetic Variation: Informative |
| | DNA Sequence | ANSI/HL7 V3 CGPED, R1-2007 |
| | Microarray Data | MIAME, MAGE-ML |
| | MiRNA Expression | HL7 V3 CG GV, R1 |
| | Chromosomal Copy # | HL7 V3 CG_GENO, R1-2007 (DSTU) |
| | Loss of Hertrozygocity | XML schema (GMD) |
| | Methylation Patterns | OMIM, GO |
| | Nucleotide Sequence | SAM, ASN.1 |
| | Sequence Variation | GSVML |
| | Family Genetic Data | Pedigree: Normative, ANSI |

TABLE 4

Data and Standards - Trialotypic Data Service Unit

| Data Type | Content Exchanged | Key Standards |
| --- | --- | --- |
| Trialotypic Data | Biographic Data | HL7 |
| | Eligibility | CDISC |
| | Concurrent Therapy | DRG |
| | Assessment Test | CPT-4 |
| | Adverse Events | HCPCS |

TABLE 5

Data and Standards - Proteotypic Data Service Unit

| Data Type | Content Exchanged | Key Standards |
| --- | --- | --- |
| Proteotypic Data | Biographic Data | HL7 |
| | Gene Fusion | PSI-MI |
| | Phylogenetic Profiles | MIAPE |
| | Ortholog Interaction | PSI-MI |
| | Domain Interaction | PSI-MI |

TABLE 5-continued

Data and Standards - Proteotypic Data Service Unit

| Data Type | Content Exchanged | Key Standards |
|---|---|---|
| | Microarray Gene Co-expression | PSI-MI |

TABLE 6

Data and Standards - Pathotypic Data Service Unit

| Data Type | Content Exchanged | Key Standards |
|---|---|---|
| Pathotypic Data | Biographic Data | HL7 |
| | Enzyme Records | BioPax |
| | Metabolic (Biological) Pathways | BioPax |
| | Non-Metabolic Pathways | BioPax |
| | Networks of Metabolic Pathways | BioPax |
| | Networks of Non-metabolic Pathways | BioPax |
| | Functional Hierarchies | BioPax |
| | Biological Processes | SBML |

TABLE 7

Data and Standards - Theratypic Data Service Unit

| Data Type | Content Exchanged | Key Standards |
|---|---|---|
| Theratypic Data | Biographic Data | HL7 |
| | Genes | NDC |
| | Drugs | RxNorm, NDF-RT, NCPDP, CCR |
| | Diseases | ICD-9-CM/10, CCS, SNOMED CT |
| | Interventions | HL7 CDA Release 2, CCD |

Metadata may be formed by aggregating data according to the above data types, as summarized in Table 8.

TABLE 8

Data and Standards - Metatypic Data Exchange Unit

| Data Type | Data Sources | Key Standards |
|---|---|---|
| Metatypic Data | 1. Phenotypic Data Service Unit | HL7 Version 2,3 |
| | 2. Genotypic Data Service Unit | ADT |
| | 3. Trialotypic Data Service Unit | CCOW |
| | 4. Proteotypic Data Service Unit | EDI Exchange Formats |
| | 5. Pathotypic Data Service Unit | IEEE 1073 |
| | 6. Theratypic Data Service Unit | XDS, NCPD (X12N) |
| | | MTOM |
| | | SAML |
| | | SOAP |
| | | UDDI |
| | | WS-Addressing |
| | | WSDL |
| | | WS-Security |
| | | XMI |
| | | XML Schemas |

Aspects of aggregating and exchanging metadata according to the above standards will be discussed in further detail in later sections. Clinical scenarios in which the above data standards may be leveraged are now discussed.

Exemplary Clinical Scenarios

As a first non-limiting example, a hospital has been running a large, pharmaceutical sponsored clinical trial for lung cancer that has been approved by the Institutional Review Board (IRB). The mechanism of action of the compound is not precisely known and a limited sub-set of patients are showing efficacy. Several patients enrolled in the study are experiencing side effects. An oncologist involved in the trial has discussed this with an oncology fellow and asked the fellow to investigate if the adverse effects or compound mechanism of action can be identified. The medical informatist has questions about this case: What data types are leveraged in this scenario? What standards are associated with these data types? Data leveraged in this example may include Clinical Data (CDA), Gene Expression (MAGE), Clinical Trial (ODM), Mutation Data (BSML), Genotype (HapMap), Unstructured Text (PubMed) and dbSNP. One must keep in mind also the enabling standards related to those data type to be communicative.

As a second non-limiting example, a 37-year-old HIV-infected woman on antiretroviral therapy has a previous history of virologic failures. She is treated in a medical care hospital that has an electronic medical record system. She is on numerous medications and was admitted this time to the hospital with fever, anorexia, weight loss, and gastrointestinal symptoms. Clinical examination revealed skin lesions similar to Kaposi's Sarcoma. Diagnostic biopsy confirmed bacillary organisms. Her CD4 count is 127 cells/mm3 and HIV RNA 35,37 copies/ml. An HIV resistance test is ordered. The treating physician has questions about this case: Could the phenotypic assay correlated with the genotypic assay? Could the genotypic assay detect an association with her cancer? Could there be a relevant clinical trial study that investigated HIV drug resistance? Could the protein-protein interaction assay analysis identify a new therapeutic approach? Could the disease pathways assay analysis identify of proteotoxicty? Could there be a personalized therapy? Are there any drug-drug interactions?

It should be appreciated that in both exemplary scenarios, the questions posed necessitate access to various data types, which typically exist in heterogeneous systems, thereby preventing researchers and practitioners from unlocking potential personalized research and treatments. Technically, administration of individual systems is increasingly difficult. It involves hundreds of configurations, tuning parameters for databases, web application servers, and data storage. Heterogeneous systems are becoming increasingly connected. Therefore, integration is becoming even more difficult and IT architects cannot intricately cope with the data interactions among different components. A practical solution to the existing knowledge management crisis in healthcare research is the adoption of new innovative research methods. This could be achieved by using the HIVE BIOMED SYSTEM research-based knowledge management and discovery technology, which could enhance research capabilities in biomedicine and untimely demonstrate their potential benefit to patient care. In particular, providing researchers and healthcare providers near real-time access to longitudinal patient metadata as discussed herein facilitates biomedical research discovery and innovation beyond that which is currently available.

Exemplary Architectural Framework Model

Figure 7:
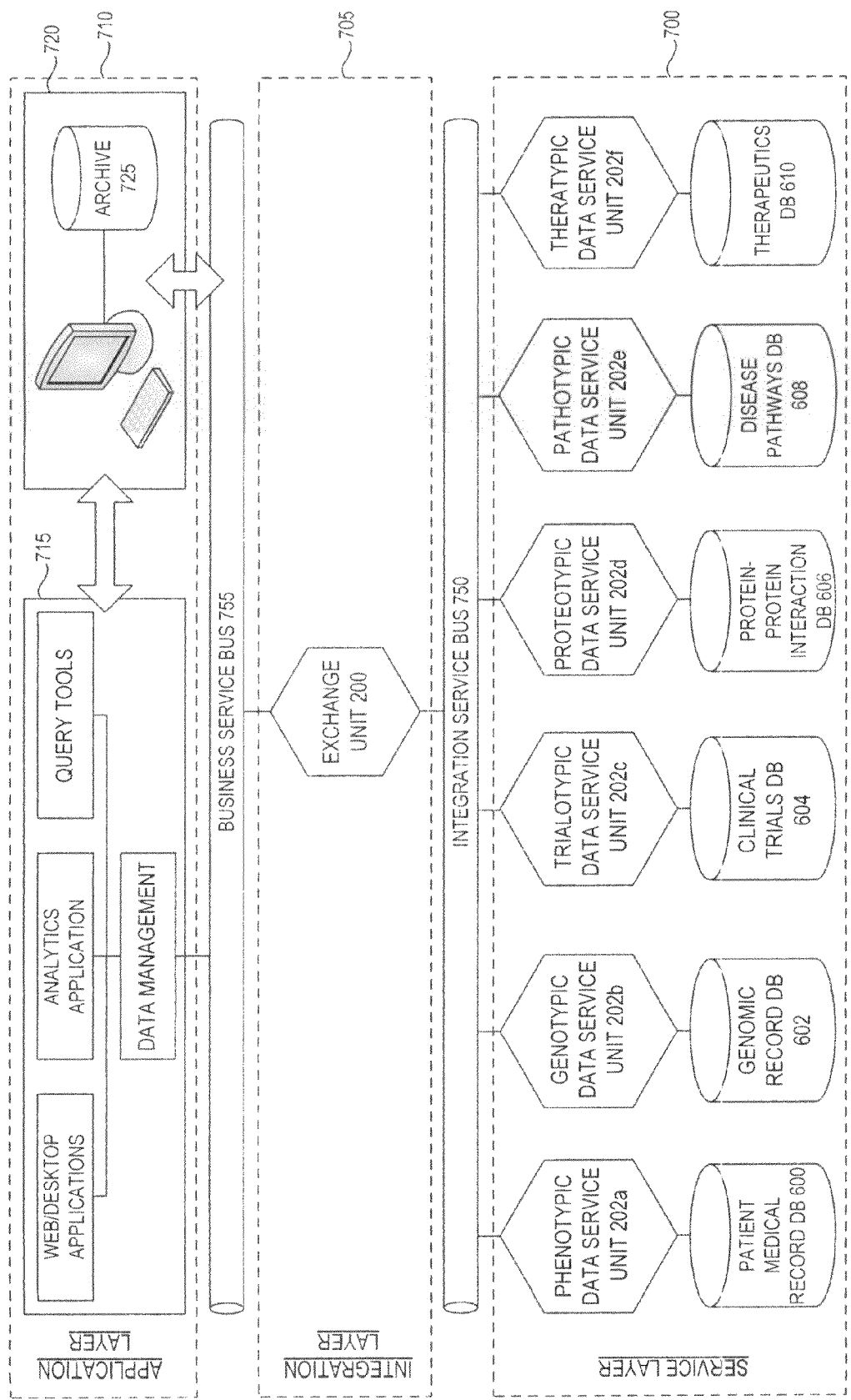
FIG. 7 illustrates an exemplary architectural framework model according to one aspect of the present disclosure.

Next, FIG. 7 illustrates an exemplary architectural framework model for the HIVE device 100 according to one aspect of the present disclosure. It is noted that while the exemplary framework of FIG. 7 is described with respect to the HIVE device 100, it should be appreciated that aspects of the framework may be adapted to other elements/devices connected with the HIVE BIOMED SYSTEM 1. In certain embodiments, the exemplary framework of FIG. 7 may correspond to a personalized research hub.

In the exemplary architecture of FIG. 7, there are three architecture layers of HIVE device 100, which are considered the backbone of the enterprise architectural framework. The three architecture layers of FIG. 7 include a service layer 700, an integration layer 705, and an application layer 710. Detailed descriptions of these three layers, and the interaction thereof, follows below.

First, the service layer 700 includes the six service units 200a-f that contain aggregates of relevant minimum data required, wherein the data is derived from each respective service unit's corresponding data repository (i.e., databases 600 to 610). In one aspect of the present disclosure, each repository is linked to a corresponding open-source software/application. In brief, the service layer 700 is where data abstraction and aggregation occurs in the HIVE device 100. In certain aspects of the present disclosure, dedicated open-source applications (e.g., open-sourced applications) on the service units 202a-f send messages (e.g., XML-based) containing predetermined sets of minimum data elements to their corresponding data repositories (databases 600 to 610). Data is abstracted (moved) from the assigned resource repositories to be aggregated within their own service unit. The data moved from the repository may be of one or more of the standards listed above in Tables 2-7, or of another standard. Because the service layer 700 is considered that gate of the exemplary enterprise architecture, data governance and security measures should be smartly deployed.

Next, in the non-limiting example of FIG. 7 the integration layer 705 includes the exchange unit 200. In this example, the integration layer 705 is the architecture layer in which metadata integration occurs. In certain aspects of the present disclosure, the exchange unit 200 may be configured to exchange aggregated metadata from each personalized research hub with another exchange unit of a different hub (i.e., patient). When executing metadata integration processing, elements included in the integration layer 705 may execute open-source application and integration tools. Processing in the integration layer 705 may be executed such that data of various standards may be exchanged.

Next, in the non-limiting example of FIG. 7 the application layer 710 provides the data management and analytics layer wherein labeled data may be orchestrated and readily available for analytical services. Advanced query tools may be deployed and operated in this layer. Open-source data mining applications may also be deployed in this layer for analytics and data mining. Analytics presentation section 715 is shown in the figure to represent various analytical tools that may be utilized in the application layer 710. The exemplary tools of the analytics presentation section 715 may include data management tools, web/desktop applications, analytics applications, and query tools, which may all be built on the previous layers for robust analysis of the information derived from the processes of the service layer 700 and the integration layer 705.

An interface 720 may additionally run in the application layer 710. In certain embodiments, the interface 720 may provide the structure on which the analytics presentation section 715 may execute its various tools and analysis applications. The interface 720 may include an archive 725, which may be configured to store, e.g., query results returned from the HIVE BIOMED SYSTEM 1. In certain aspects of the present disclosure, the interface 720 may also output updated patient information to the HIVE BIOMED SYSTEM 1 such that a patient's personalized research hub (i.e., the patient's corresponding exchange unit 200) may be updated to reflect changes (e.g., new treatment received).

In order for three architectural layers in the exemplary model to operate, they are interconnected using an enterprise service bus approach. In particular, the exemplary model includes two enterprise service buses: integration service bus 750 and business service bus 755. The integration service bus 750 connects the service layer 700 with the integration layer 705. In certain aspects of the present disclosure, the integration service bus 750 acts as service-driven and standards-based messaging engine, and provides a data integrative layer on top of the service units 202a-f that will transform integration into business services. The business service bus 755 connects the integration layer 705 with the application layer 710. In certain aspects of the present disclosure, the business service bus 755 acts as an integration-driven and standardized messaging engine, and provides a business-based layer on top of the exchange units 200 that will transform business services into business processes. The business service bus 755 may additionally ensure seamless data orchestration for advanced data mining, research intelligence, and knowledge discovery.

In another embodiment, the model of FIG. 7 may be adapted to include an additional inter-enterprise service bus deployed on top of the business service bus 755 and between the interface 720 and the analytics presentation section 715. This adaptation may be applicable for implementation, e.g., in a large-scale medical organizations having several remote research facilities.

Openness of Architecture Framework

In certain aspects of the present disclosure, the HIVE BIOMED SYSTEM 1 may employ an open-source application framework. For example, tools included in the analytics presentation section 715 of FIG. 7 may be open-source applications. The HIVE BIOMED SYSTEM 1 may be built on open-source standards, where its framework allows for open-source software to run on top of its architecture. Open-source is a framework that allows open-source software (OSS) to run on top of its architecture. In other terms, whenever there is an OSS running on a framework, this gives the feature of the openness of the application.

Open-source application frameworks use open-source methods, such that anyone can use, copy, and modify the software. Moreover, contributors can provide enhancements that result in open source collaborative development, which will lead to research exchange community. Therefore, open source tools make it easier for research institutions to compete for innovation. Most open-source software is based on Java, which is platform independent, which allows open-source and licensed (closed-source) software to co-exist and work in harmony on the same platform. Other known examples to open-source application are Apache Web Server project and community driven open-source middleware.

Certainly, the availability of quality support is very important when choosing between open-source or licensed. Nowadays, open-source software is reliable and has high-quality of support. The advantage is that with open-source software no support fee is required, in addition no need for license for every employee that uses the software. Thus, investment in open-source is always less and therefore, the return on investment (ROI) is realized rapidly.

The HIVE BIOMED SYSTEM 1 may interface with an ontology application. There are only few open-source ontology applications that are used in biomedical research. A careful analysis of these applications resulted in choosing "Protégé" to be the preferred ontology hub for the HIVE BIOMED SYSTEM 1. Protégé is a free, open-source (Java tool) ontology editor that provides an extensible architecture for the creation of customized knowledge-based applications. Protégé can be extended by Java-based Application Programming Interface (API) to build knowledge-based tools and applications. It also, enables users to build ontologies in the W3C's Web Ontology Language (OWL). While Protégé is the preferred ontology editor for the HIVE BIOMED SYSTEM 1, it should be appreciated that this is not limiting, and other ontology application may be used within the scope of the present disclosure.

Service-Oriented Architecture

In certain aspects of the present disclosure, the HIVE BIOMED SYSTEM architecture may utilize SOA principles. SOA is "a philosophy of design where a toolset of mix-and-match units ("services"), each performing a well-defined task, can reside on different machines (including geographically separated ones) and be ready to be used when needed" [52]. Web services are considered to have the most widespread implementations of SOA given the extensibility of XML messages that moves over Hypertext Transfer Protocol Secure (HTTPS).

More important of than the definition of what SOA is, is the question of what SOA is not. SOA is neither software, nor a middleware, nor an enterprise service bus, nor products. Thus, SOA is not an out-of-the-box solution and therefore, a pragmatic step-by-step approach is needed to identify processes and governance issues. The concept of SOA is rapidly emerging as the premier integration and framework in today's complex, heterogeneous computer-based environments in most industries. Notably, the health care industry is considered to be a slow adaptor of SOA technologies.

The followings are considered to be compelling technology-oriented definitions of SOA. IBM defines it as "SOA is an application framework that takes applications and breaks them down into individual functions and processes, called services. It lets you build, deploy and integrate these services independent of applications and the computing platforms on which they run" [53]. Likewise, Sun Microsystems of Oracle defines SOA as "an architectural style that emphasizes well-defined, loosely coupled, coarse-grained, business-centric, reusable shared services" [54]. Therefore SOA should be looked at as an architectural style or distinctively as an application framework.

Advantages of SOA:

One aim of the HIVE BIOMED SYSTEM, according to certain aspects of the present disclosure, is to build a research platform as an accurate and scalable system, incorporating the research into parallel moveable software modules within flexible system architecture. The main technical advantage of SOA that it is based on open standards such as Web Service Definition Language (WSDL), XML, Simple Object Access Protocol (SOAP), Universal Description Discovery and Integration (UDDI), and Business Process Execution Language (BPEL). The SOA framework adds a great value to any healthcare legacy by utilizing system resources while enhancing interoperability within and between healthcare organizations.

The main values of SOA from IBM perspective, is the ability to develop flexible models that are enabled by increased granularity of processes ("services"), reuse prebuilt service components, integrate disconnect systems, offer new services regardless of the underlying IT infrastructure and improve visibility into critical business operations [55]. Recently, web services took the flexibility of SOA to a whole new level by introducing open standards. Thus, services can be combined and recombined to meet demands and changes dynamically.

In summary, SOA enables users to bridge and access information silos in an enterprise application in an efficient and effective way. It allows architects to create modernistic solutions in real-time enterprise for research discovery. Furthermore, SOA is about transforming a silo-oriented framework to service-oriented environment. Therefore, it encompasses process, practice, platform, and people. To conclude, a fair amount of research was conducted to explore the role of SOA in healthcare IT industry [56, 57, 58]. Thus, the healthcare industry could achieve significant results through the benefit realization and the adoption of SOA technology.

Figure 8:
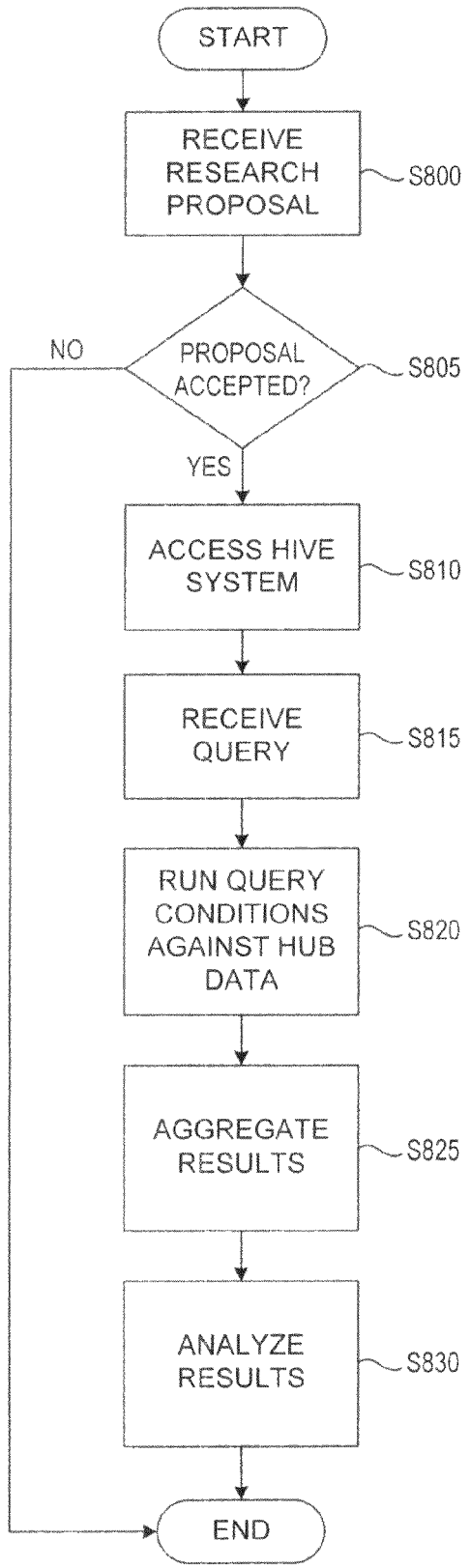
FIG. 8 illustrates a non-limiting example of an algorithmic flowchart illustrating HIVE BIOMED SYSTEM processing.

Exemplary Methods for Personalized Biomedical Medical Information Research Analytics and Knowledge Discovery Next, FIG. 8 illustrates a non-limiting example of an algorithmic flowchart illustrating HIVE BIOMED SYSTEM processing.

Referring to the flowchart, the HIVE BIOMED SYSTEM 1 at step S800 receives an input corresponding to a research proposal. In response to receiving the research proposal input at step S800, the HIVE BIOMED SYSTEM 1 at step S805 determines whether the proposal meets IRB oversight regulations. In certain embodiments, IRB approval is gained by forwarding the research proposal to an external system, in which case the HIVE BIOMED SYSTEM 1 may transmit the request and receive an approval notice. If approval is not obtained at step S805, the processing ends.

Otherwise, following receipt of IRB approval, the user is provided access to the HIVE BIOMED SYSTEM 1. Access may be provided, e.g., by verifying user identity, proper credentials for system access, etc. After granting system access, the user may submit queries to the HIVE BIOMED SYSTEM 1. Queries received by the HIVE BIOMED SYSTEM 1 may, in certain embodiments, correspond to information requests for all patients meeting a predetermined search criteria and/or filter conditions. Search criteria and/or filter conditions may be selected via a user interface. Non-limiting examples of search criteria and filter conditions that may be set in a query request include data corresponding to the "content exchanged" column in Tables 2-7. Further, a user may desire information corresponding to a subset of service units connected with exchange units on the HIVE BIOMED SYSTEM 1 network. For example, the user may set filter conditions such that only information from identified service units 202 is provided in response to the query, while other service unit data is excluded from the search results (e.g., only phenotypic and pathotypic data is requested).

In response to receiving the query request, the HIVE BIOMED SYSTEM 1 transmits the request to one or more other devices on connected on the HIVE BIOMED SYSTEM 1 network. In certain embodiments, the query request is transmitted to one or more exchange units connected to the HIVE network. Using the exemplary network overview illustrated in FIG. 1, a query request may originate at the HIVE device 100, in which case the query request is transmitted to the provider server 102 and/04 the research server 104. In broader terms, the query request may originate from a personalized research hub (i.e., from a hub's exchange unit) in a personalized research network, and the query request may be sent to one or more other personalized research hubs on the personalized research network. In response to receiving the query request, the personalized research hubs contrast the filter conditions and search criteria included in the query request against the metadata managed/stored at each respective hub/exchange unit. Matches may result in a patient's metadata meeting a predetermined threshold (e.g., a percentage match or confidence level) measured against the filter conditions and search criteria included in the query request.

At step S825, exchange units having matching metadata transmit their respective metadata to the exchange unit originating the query request. The originating exchange unit may then aggregate the query results at step S825 for further analysis and data mining (S830) with which to provide, e.g., a suggested course of personalized therapy. Aggregated search results may be labeled with a patient identification (ID) such that users (researchers) may identify patients, e.g., that may be desirable to be recruited in a new clinical trial (after IRB approval). Patient ID labels are preferably generic identifiers that exclude any specific Protected Health Information (PHI) as identified by the Health Insurance Portability and Accountability Act (HIPAA) that would reveal personal information corresponding to the patient without their expressed consent. Query results may be stored locally at the originating exchange unit or may be stored at a centralized data warehouse connected on the HIVE network.

Figure 9:
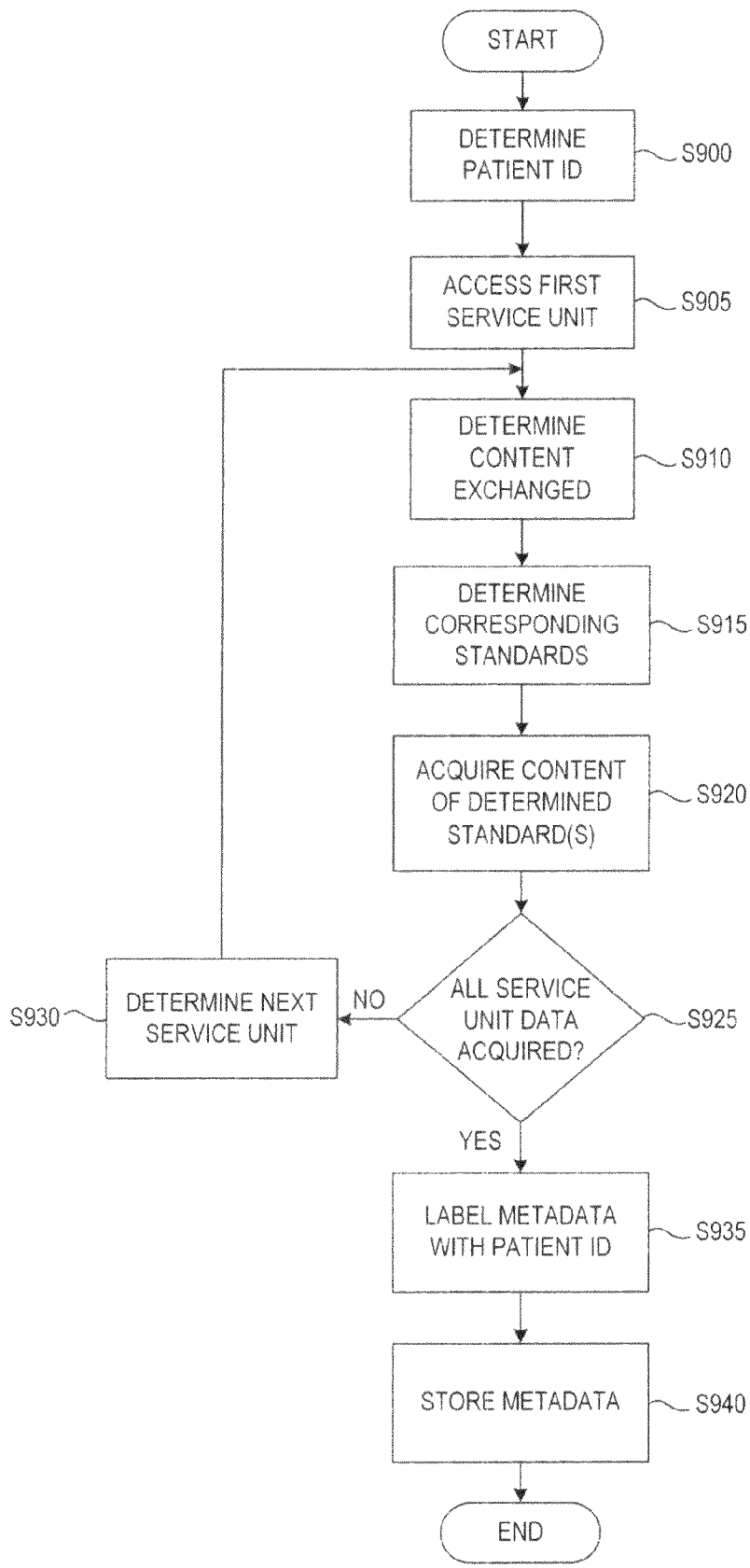
FIG. 9 illustrates an exemplary flowchart for aggregating service unit data at an exchange unit to form patient metadata.

Next, FIG. 9 illustrates an exemplary flowchart for aggregating service unit data at an exchange unit to form patient metadata.

At step S900, the HIVE BIOMED SYSTEM 1 determines a patient ID corresponding to the personalized research hub at which the metadata will be aggregated within the hub's exchange unit. As mentioned previously, the patient ID may be a generic tag (e.g., an alphanumeric code) corresponding to a particular patient. Aggregated metadata may be labeled within the exchange unit, and the metadata may subsequently transmitted with the tagged patient ID for tracking and patient linking by other users.

At step S905, the exchange unit accesses the first service unit from which data will be aggregated to form the patient metadata. In the examples discussed herein, six service units provide data to form the metadata; however, this is not limiting and aspect of the present disclosure may be adapted such that any number of service units (or a subset thereof) provides data to form the metadata.

At step S910, the exchange unit determines the content exchanged by the service unit from which data is currently being derived. For example, the exchange unit 200 may acquire phenotypic data from the phenotypic data service unit 202a at step S910. In this case, the exchange unit may determine the content classifications of the data stored/managed by the phenotypic service unit 202a (e.g., the listing of "content exchanged" in Table 2). The content exchanged classifications may, in certain embodiments, be determined in advance. In other embodiments, the exchange unit may query the service unit (or another external device on the network) to determine the content classifications managed/stored by the service unit.

At step S915, the exchange unit determines data standards corresponding to the content exchanged by the service unit, and acquires the content of the determined standard(s) at step S920 to form patient metadata. In the above example relating to the phenotypic data service unit 202a, the exchange unit 200 may determine corresponding data standards for each of the content exchanged classifications determined at step S915. That is, the exchange unit may determine, e.g., that the data standards listed in the "key standards" column of FIG. 3 respectively correspond to the content exchanged classifications for the service unit. The exchange unit 200 may acquire the service unit data of disparate standards from the service unit's corresponding data repository (e.g., patient medical record DB 600). The corresponding data standards for a service unit may, in certain embodiments, be determined in advance. In other embodiments, the exchange unit may query the service unit (or another external device on the network) to determine the data standards managed/stored by the service unit.

At step S925, the exchange unit determines whether data from all service units has been acquired. If not, the exchange unit at step S930 determines the next service unit from which to acquire data, and the above process is iterated for each service unit included in a personalized research hub. Taking the personalized research hub of FIG. 6 as exemplary, the exchange unit 200 may acquire data of disparate standards from each of the service units 202a-f to form the patient metadata using the above-described method.

At step S935, the exchange unit labels the patient metadata derived from the service unit content with the corresponding patient ID, and the metadata is stored at step S940. In certain embodiments, local or centralized data repositories may be utilized for storing the patient metadata corresponding to a patient's personalized research hub. For example, referring to FIG. 1, the database 108 may store patient metadata for all patients under the care of the healthcare provider connected to the healthcare provider network 2, and the patient data may be accessed and exchanged between other networks in the HIVE BIOMED SYSTEM 1.

Figure 10:
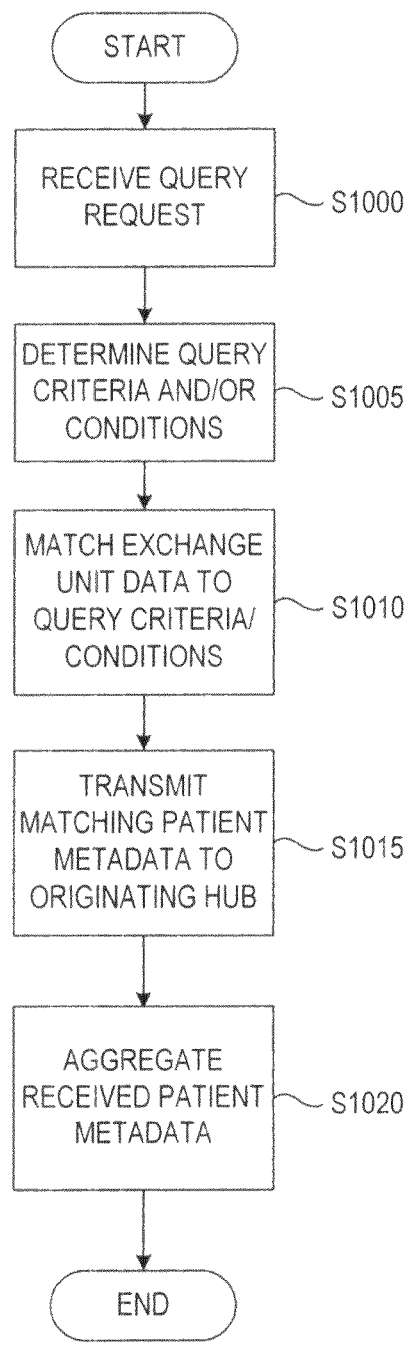
FIG. 10 illustrates an exemplary flowchart for exchange unit communication processing.

Next, FIG. 10 illustrates an exemplary flowchart for exchange unit communication processing according to one aspect of the present disclosure. It should be appreciated that while the present example is discussed with regard between two exchange units (i.e., an originating hub and a receiving hub), the skilled artisan will easily appreciate that the exemplary processing of FIG. 10 may be performed serially or concurrently on any number of devices, and subsequently data may be exchanged across a network between all devices or a subset thereof (e.g., from all receiving hubs to the originating hub, from exchange hubs to central and/or local data repositories, etc.).

Referring now to the figure, at step S1000, a receiving exchange unit of a personalized research hub receives a query request, e.g., from another originating exchange unit (or personalized research hub) connected in a network with the HIVE BIOMED SYSTEM 1. The query request may be similar to those discussed above at least with respect to FIG. 8.

In response to receiving the query request, the receiving hub exchange unit determines the query request filter conditions and/or search criteria at step S1005. In certain aspects of the present disclosure, the filter conditions may correspond to data of a particular type (i.e., from a particular service unit classification), and the search criteria may correspond to content classifications for the datasets stored on service units. As a non-limiting example, the query request may correspond to a patient metadata request for all patients on the network with a particular condition (e.g., ovarian cancer), above a predetermined age, from a particular geographic region, and having past experience with a particular drug side effect. It is noted that the content exchanged classifications listed in Tables 2-7 may also correspond to search criteria in a query request. Filter conditions may correspond to limiting results only to particular dataset types. For example, to improve search efficiency and/or the scope of the search results, a researcher may elect to only search for data from particular data sources (i.e., service unit types), and filter conditions may be set according to the selected sources.

At step S1010, patient metadata is matched to the determined filter conditions and search criteria using a predetermined function. Matches may be determined based on aspects of the patient metadata indicating compliance with the query conditions/criteria. A predetermined threshold may be used such that only patient metadata of a predetermined relevance is returned in response to the query request. Alternatively, the originating hub may order query results based on relevance to the defined query conditions/criteria.

At step S1015, the receiving hub transmits the matching patient metadata to the originating hub. Since patient metadata is typically received from a plurality of receiving hubs, the originating hub at step S1020 aggregates all the received patient metadata, and further analysis may then be performed based on user need.

As a non-limiting example, FIGS. 11A and 11B illustrate an exemplary process of performing extra hub data exchange from one metatypic core exchange unit with another metatypic core exchange unit (FIG. 11A) and an exemplary process of performing extra hub data integration among metatypic core exchange units in the HIVE BIOMED research network (FIG. 11B), whereby the example of FIGS. 11A and 11B may correspond to the flowchart of FIG. 10.

Database Model—High Level Schema

Figure 12A:
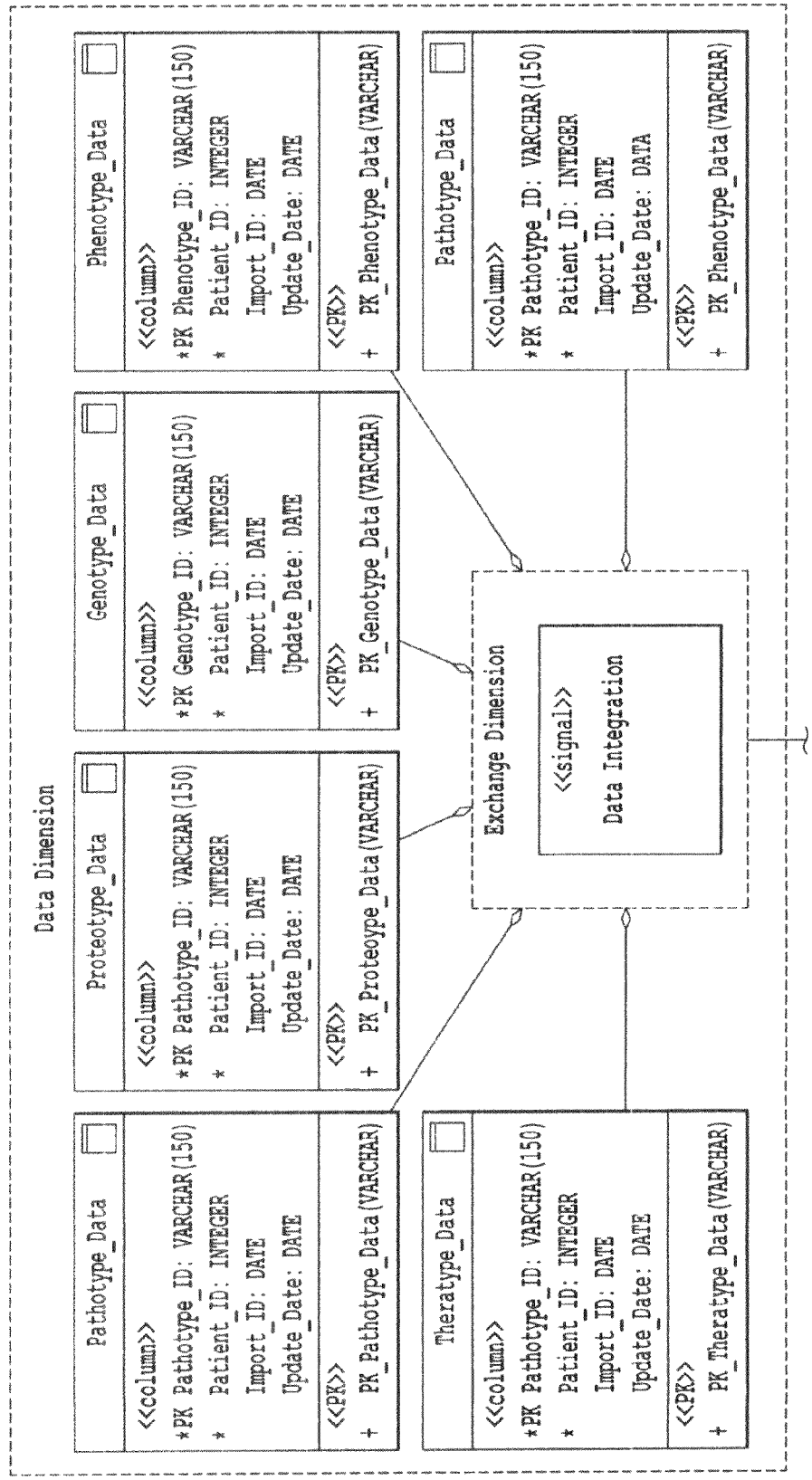
FIGS. 12A-12C illustrate an exemplary relational database model of a personalized research hub according to one aspect of the present disclosure.
Figure 12B:
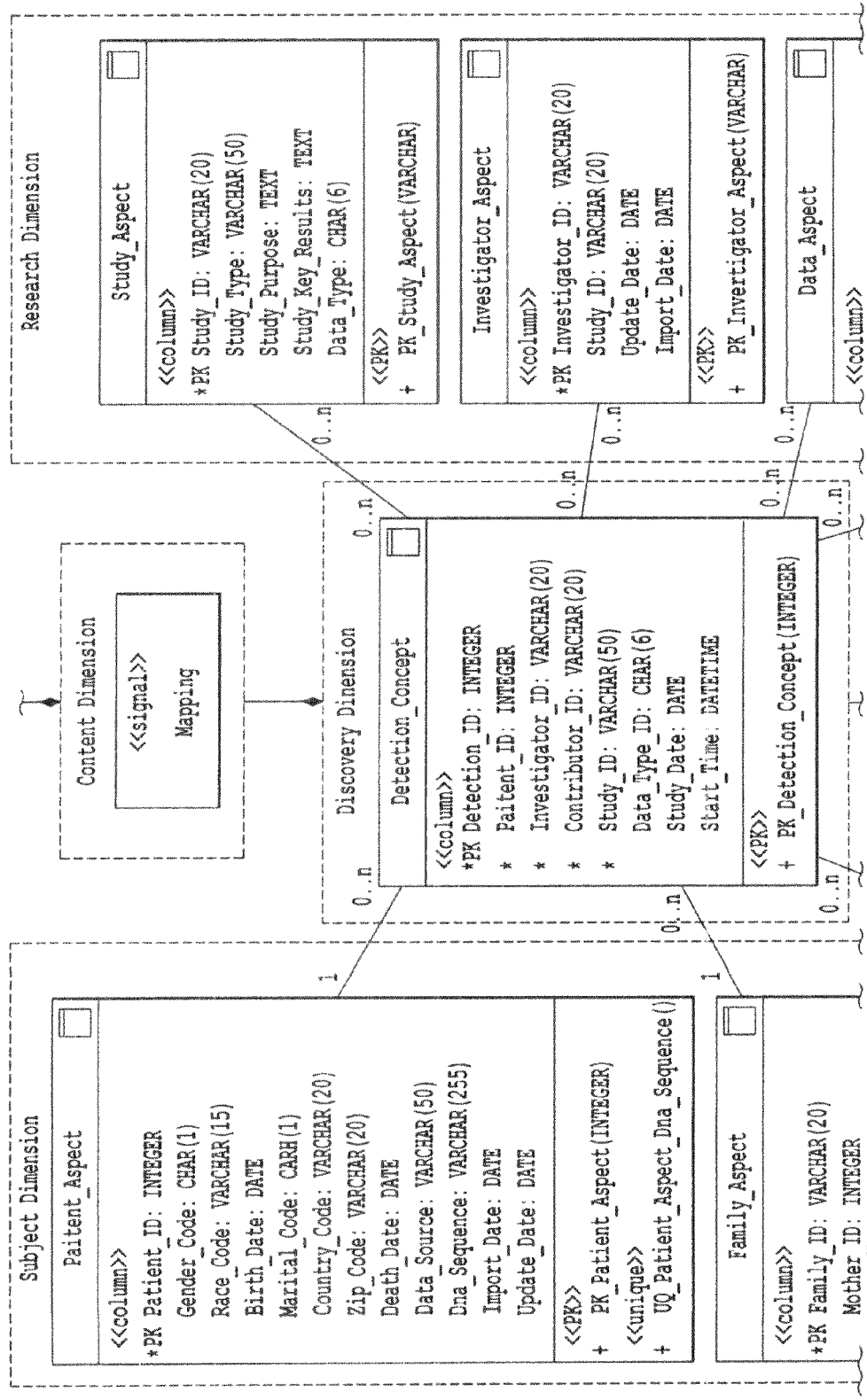
Figure 12C:
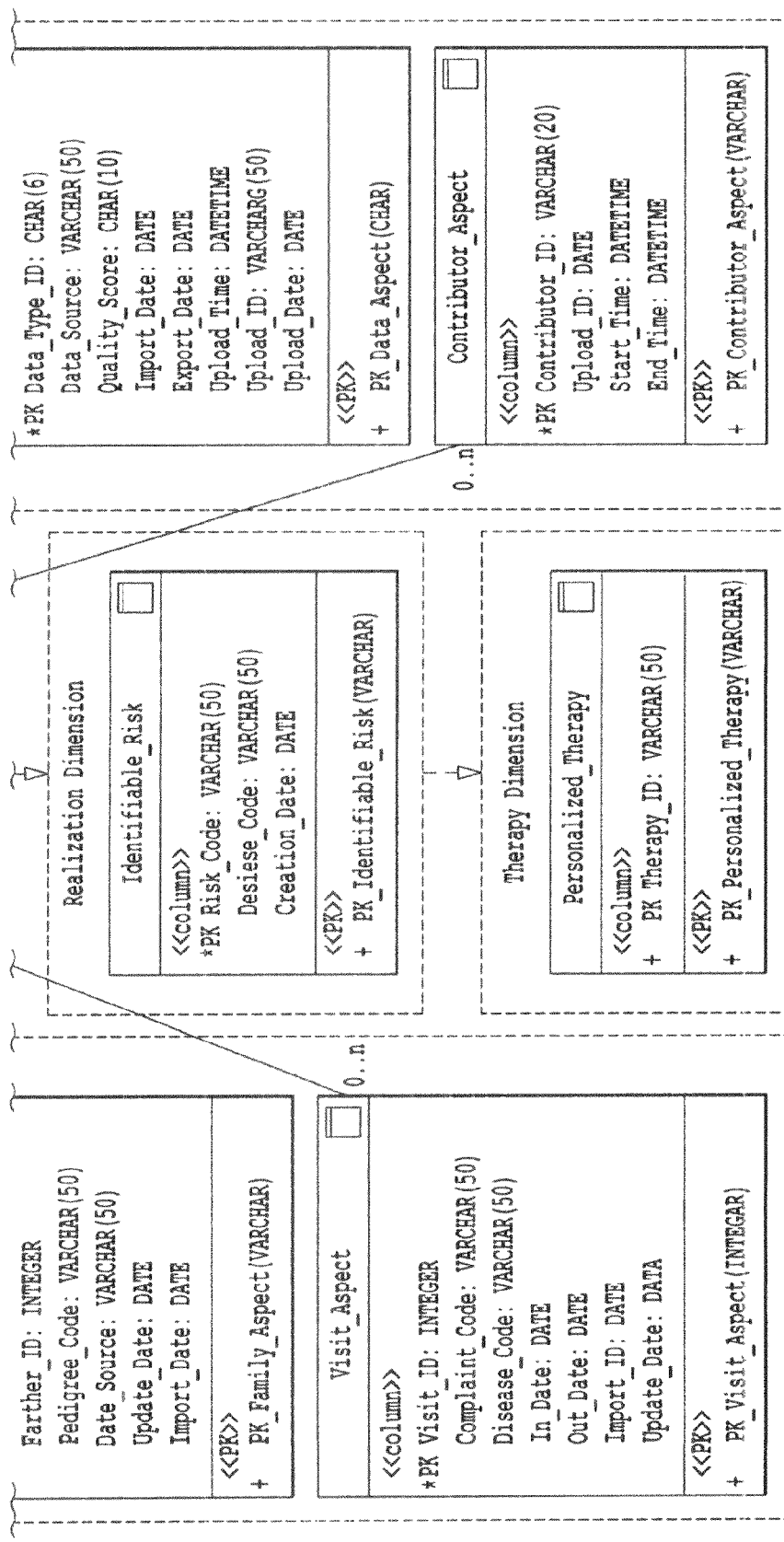

Next, FIGS. 12A-12C illustrate an exemplary relational database model of the personalized research hub according to one aspect of the present disclosure. The dimensional modeling of the schema in FIGS. 12A-12C consists of several parameters. Factual data can be queried using a variety of contextual dimensions, which are clusters of descriptors that define the data facts.

The database model consists of two main dimensions, which are the data dimension and the discovery dimension. In certain aspects of the present disclosure, the data dimension encompasses the six service units and the exchange unit of the personalized research hub. The data dimension sub-models are linked to the class data model, where data is derived as "get_Attribute" in accordance to its related data standard. The exchange dimension exchanges data contextually with the discovery dimension as needed.

The discovery dimension consists of two main sub-models, which are the subject dimension and the research dimension. They both directly interact with the discovery dimension in order to identify risk factors by utilizing the realization dimension, which ultimately activates the therapy dimension for therapeutic options.

Discovery Process

Figure 13:
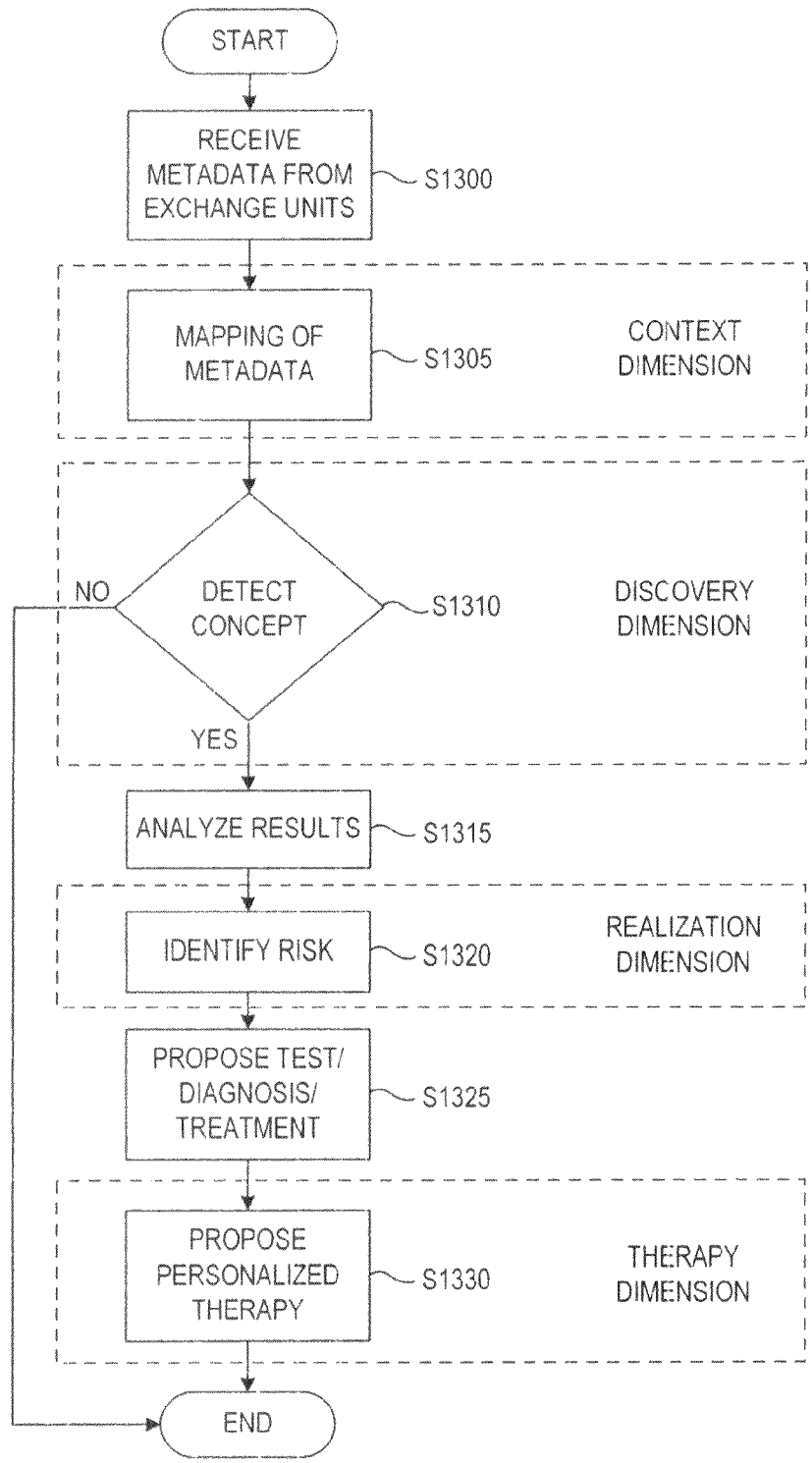
FIG. 13 illustrates a non-limiting example of an algorithmic flowchart for a discovery process according to one aspect of the present disclosure.

Next, FIG. 13 illustrates a non-limiting example of an algorithmic flowchart for a discovery process according to one aspect of the present disclosure. It is noted that the flowchart of FIG. 13 includes exemplary dimensions corresponding to the database model of FIGS. 12A-12C.

Referring to FIG. 13, the HIVE BIOMED SYSTEM 1 at step S1300 receives metadata from one or more other exchange units connected on a common network. At step S1305, the HIVE BIOMED SYSTEM 1 performs mapping of the received metadata. In one aspect of the present disclosure, step S1305 corresponds to the context dimension of the above-described database model. At step S1310, the HIVE system 1 determines whether a concept is detected. In one aspect of the present disclosure, step S1310 corresponds to the discovery dimension of the above-described database model. If a concept is detected at step S1310, the HIVE BIOMED SYSTEM 1 analyzes the results at step S1315. Otherwise, the process ends. At step 1320, the HIVE BIOMED SYSTEM 1 identifies risk based on the analyzed results. In one aspect of the present disclosure, step S1320 corresponds to the realization dimension of the above-described database model. At step S1325, the HIVE BIOMED SYSTEM 1 suggests at least one of a test, a diagnosis, and a treatment. At step S1330, the HIVE BIOMED SYSTEM 1 proposes a personalized therapy. In one aspect of the present disclosure, step S1330 corresponds to the therapy dimension of the above-described database model.

Exemplary User Interface

Figure 14:
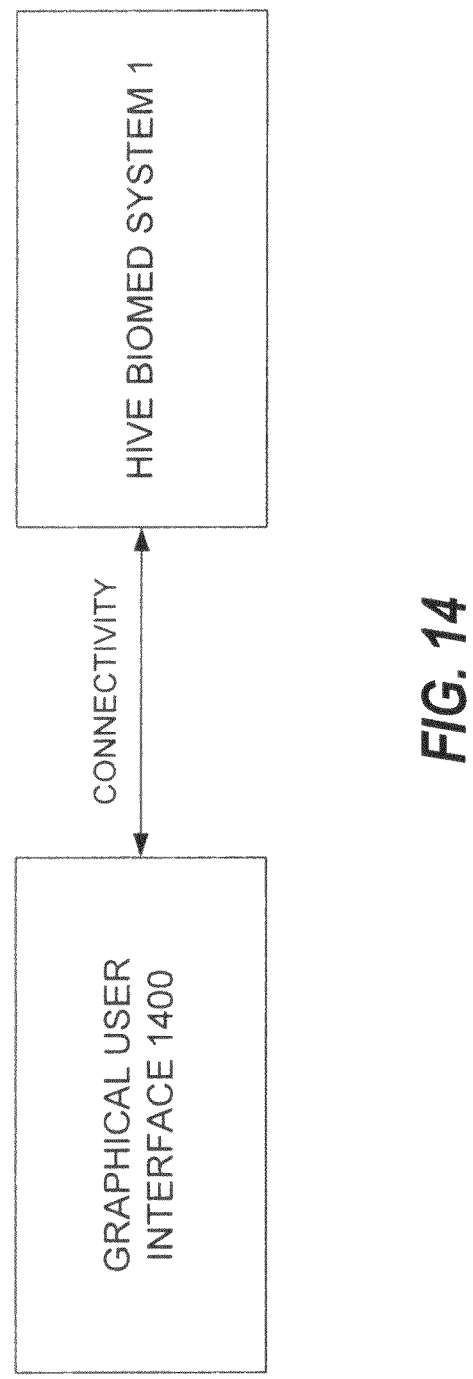
FIG. 14 illustrates connectivity between the HIVE BIOMED SYSTEM and a graphical user interface according to one aspect of the present disclosure.
Figure 15:
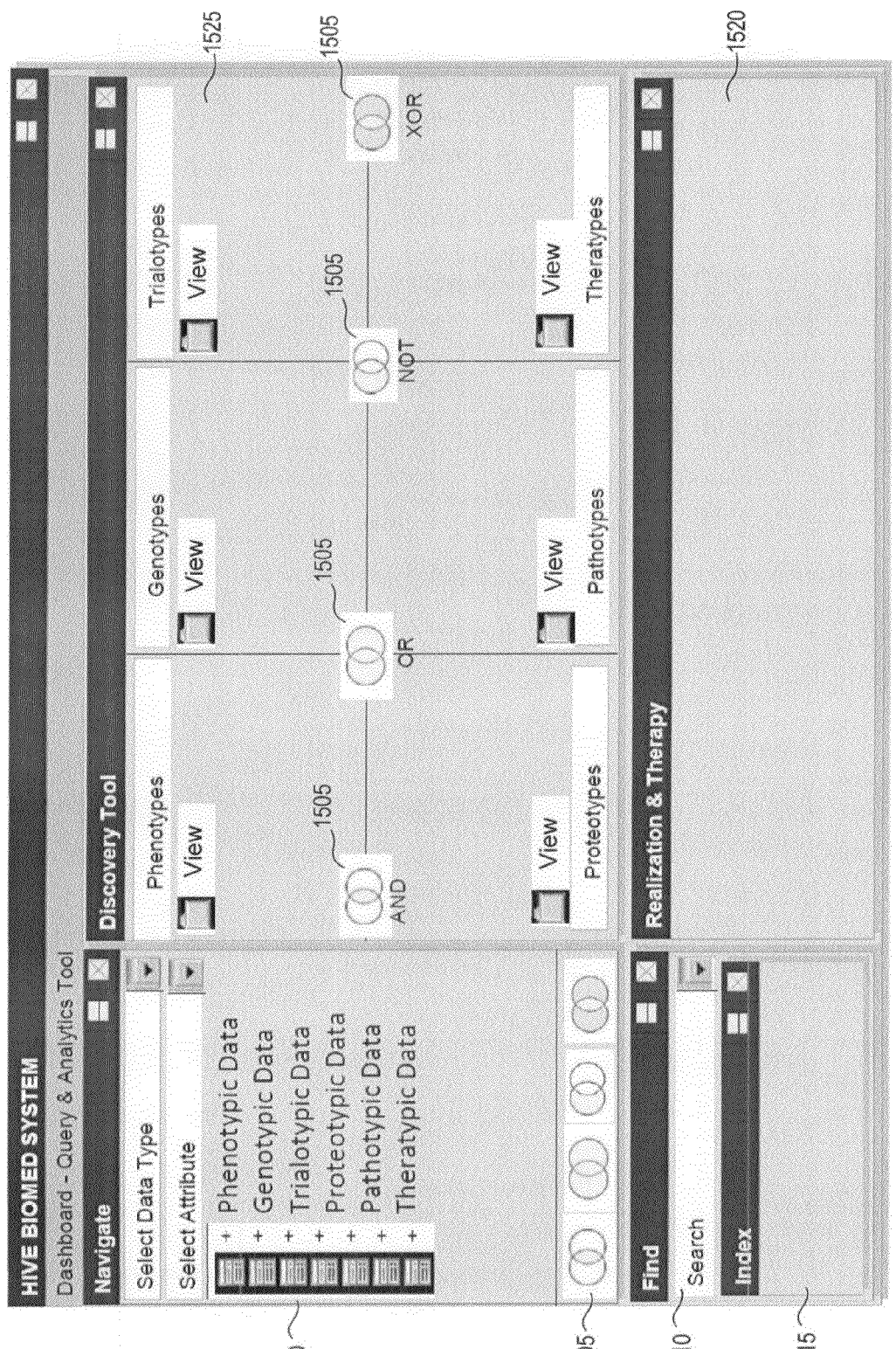
FIG. 15 provides a non-limiting example of the graphical user interface according to one aspect of the present disclosure.

Next, FIG. 14 illustrates connectivity between the HIVE BIOMED SYSTEM 1 and a graphical user interface 1400, which may be provided to execute functional aspects of the present disclosure. FIG. 15 provides a non-limiting example of the graphical user interface 1400. Various interface tools are included in the graphical user interface 1400 to execute aspects of biomedical information research analytics and knowledge discovery. Navigation tools section 1500 includes navigation functionality for each of the data types of Table 1. Boolean operators tools section 1505 includes four Boolean operator inputs options corresponding to AND, OR, NOT, and XOR. Search tools section 1510 provides search functionality. Logs may be output in the log section 1510. Problem and prescription console 1515 provides outputs, e.g., of proposed personalized therapy based on analyzed metadata received from other exchange unit on the HIVE network in response to a query.

Exemplary Hardware Embodiment

Next, a hardware description of the HIVE device 100 according to exemplary embodiments is described with reference to FIG. 16. It is noted that while this exemplary embodiment is described with respect to the HIVE device 100, aspects of this exemplary hardware embodiment may be applied to other elements of the HIVE BIOMED SYSTEM 1, and/or to elements/devices connected to the HIVE BIOMED SYSTEM 1 via a network (e.g., exchange unit 200, service unit 202).

Figure 16:
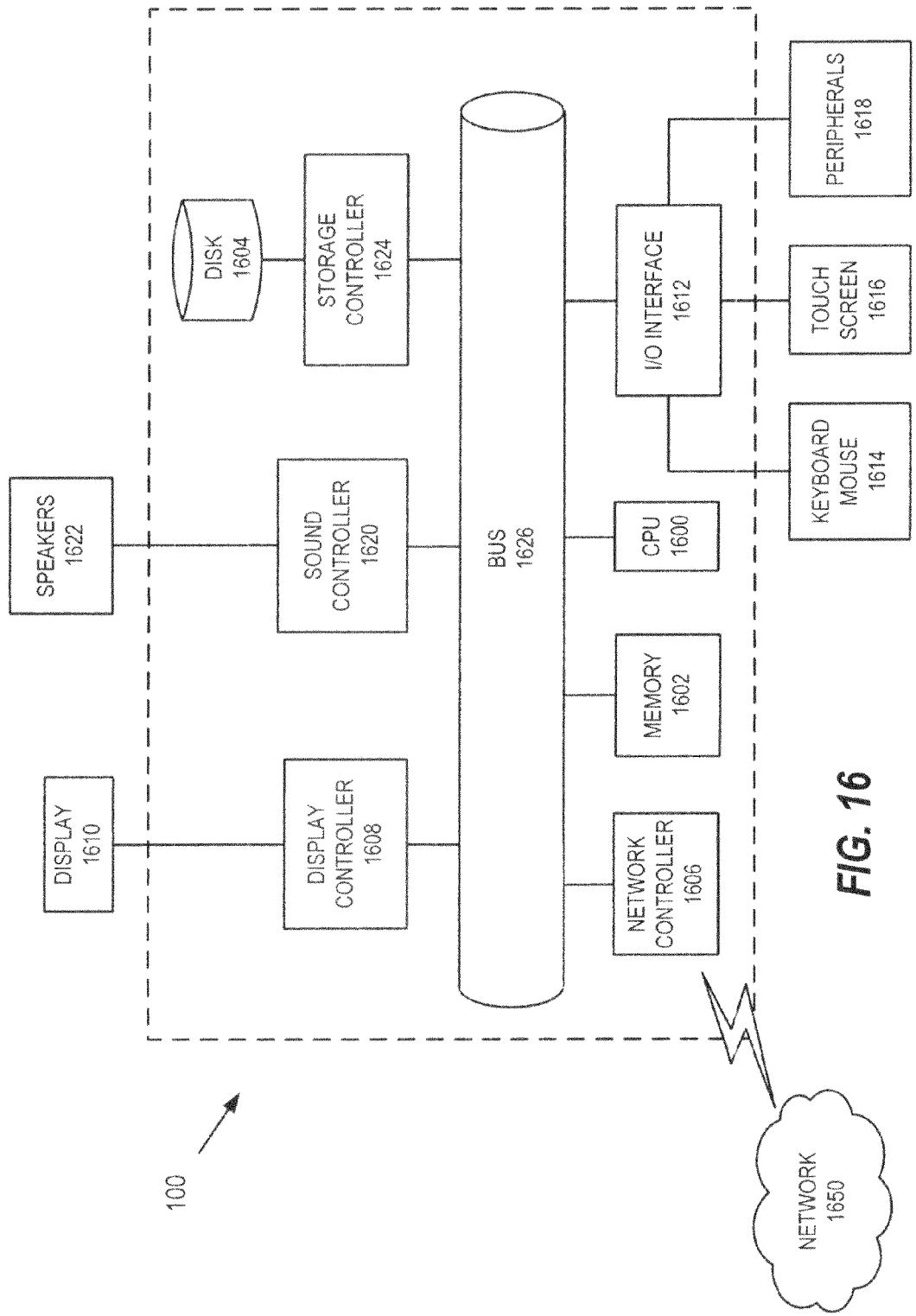
FIG. 16 illustrates an exemplary hardware embodiment according to one aspect of the present disclosure.

In FIG. 16, the HIVE device 100 includes a CPU 1600 which performs the processes described above. The process data and instructions may be stored in memory 1602. These processes and instructions may also be stored on a storage medium disk 1604 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the HIVE device 100 communicates, such as a server or computer.

Further, the claimed advancements may be provided as a utility application, background daemon, or component of an operating system, or combination thereof, executing in conjunction with CPU 1600 and an operating system such as Microsoft Windows 7, UNIX, Solaris, LINUX, Apple MAC-OS and other systems known to those skilled in the art. CPU 1600 may be a Xenon or Core processor from Intel of America or an Opteron processor from AMD of America, or may be other processor types that would be recognized by one of ordinary skill in the art. Alternatively, the CPU 1600 may be implemented on an FPGA, ASIC, PLD or using discrete logic circuits, as one of ordinary skill in the art would recognize. Further, CPU 1600 may be implemented as multiple processors cooperatively working in parallel to perform the instructions of the inventive processes described above.

The HIVE device 100 in FIG. 16 also includes a network controller 1606, such as an Intel Ethernet PRO network interface card from Intel Corporation of America, for interfacing with network 1650. As can be appreciated, the network 1650 can be a public network, such as the Internet, or a private network such as an LAN or WAN network, or any combination thereof and can also include PSTN or ISDN sub-networks. The network 1650 can also be wired, such as an Ethernet network, or can be wireless such as a cellular network including EDGE, 3G and 4G wireless cellular systems. The wireless network can also be WiFi, Bluetooth, or any other wireless form of communication that is known.

The HIVE device 100 further includes a display controller 1608, such as a NVIDIA GeForce GTX or Quadro graphics adaptor from NVIDIA Corporation of America for interfacing with display 1610, such as a Hewlett Packard HPL2445w LCD monitor. A general purpose I/O interface 1612 interfaces with a keyboard and/or mouse 1614 as well as a touch screen panel 1616 on or separate from display 1610. General purpose I/O interface also connects to a variety of peripherals 1618 including printers and scanners, such as an OfficeJet or DeskJet from Hewlett Packard.

A sound controller 1620 is also provided in the HIVE device 100, such as Sound Blaster X-Fi Titanium from Creative, to interface with speakers/microphone 1622 thereby providing sounds and/or music. The speakers/microphone 1622 can also be used to accept dictated words as commands for controlling the HIVE device 100 or for providing location and/or property information with respect to the target property.

The general purpose storage controller 1624 connects the storage medium disk 1604 with communication bus 1626, which may be an ISA, EISA, VESA, PCI, or similar, for interconnecting all of the components of the HIVE device 100. A description of the general features and functionality of the display 1610, keyboard and/or mouse 1614, as well as the display controller 1608, storage controller 1624, network controller 1606, sound controller 1620, and general purpose I/O interface 1612 is omitted herein for brevity as these features are known.

Obviously, numerous modifications and variations of the present disclosure are possible in light of the above teachings. It is therefore to be understood that within the scope of the appended claims, the invention may be practiced otherwise than as specifically described herein. For example, advantageous results may be achieved if the steps of the disclosed techniques were performed in a different sequence, if components in the disclosed systems were combined in a different manner, or if the components were replaced or supplemented by other components. The functions, processes and algorithms described herein may be performed in hardware or software executed by hardware, including computer processors and/or programmable processing circuits configured to execute program code and/or computer instructions to execute the functions, processes and algorithms described herein. A processing circuit includes a programmed processor, as a processor includes circuitry. A processing circuit also includes devices such as an application specific integrated circuit (ASIC) and conventional circuit components arranged to perform the recited functions.

The functions and features described herein may also be executed by various distributed components of a system. For example, one or more processors may execute these system functions, wherein the processors are distributed across multiple components communicating in a network. The distributed components may include one or more client and/or server machines, in addition to various human interface and/or communication devices (e.g., display monitors, smart phones, tablets, personal digital assistants (PDAs)). The network may be a private network, such as a LAN or WAN, or may be a public network, such as the Internet. Input to the system may be received via direct user input and/or received remotely either in real-time or as a batch process. Additionally, some implementations may be performed on modules or hardware not identical to those described. Accordingly, other implementations are within the scope that may be claimed.

It must be noted that, as used in the specification and the appended claims, the singular forms "a," "an," and "the" include plural referents unless the context clearly dictates otherwise.

The above disclosure also encompasses the embodiments noted below.

(1) A personalized biomedical information research analytics and knowledge discovery system comprising: an originating exchange unit including circuitry configured to transmit, to a receiving exchange unit, a query request including predetermined query criteria, and receive, from the receiving exchange unit, patient metadata corresponding to a patient; and a receiving exchange unit including circuitry configured to aggregate protein-protein interaction data from a first service unit, wherein the aggregation includes determining one or more corresponding data standards managed by the first service unit and receiving the protein-protein interaction data from the first service unit in the determined one or more corresponding data standards, generate, in response to receiving the query request, the patient metadata corresponding to the patient, and transmit, to the originating exchange unit, the patient metadata.

(2) The personalized biomedical information research analytics and knowledge discovery system of (1), wherein: the receiving exchange unit circuitry is further configured to aggregate disease pathway data from a second service unit, whereby the aggregation of the disease pathway data includes determining one or more corresponding data standards managed by the second service unit and receiving the disease pathway data from the second service unit in the determined one or more corresponding data standards, and the generated patient metadata includes the aggregated disease pathway data.

(3) The personalized biomedical information research analytics and knowledge discovery system of (1) or (2), wherein: the receiving exchange unit circuitry is further configured to aggregate therapeutics data from a third service unit, whereby the aggregation of the therapeutics data includes determining one or more corresponding data standards managed by the third service unit and receiving the therapeutics data from the third service unit in the determined one or more corresponding data standards, and the generated patient metadata includes the aggregated therapeutics data.

(4) The personalized biomedical information research analytics and knowledge discovery system of any one of (1) to (3), wherein: the receiving exchange unit circuitry is further configured to aggregate patient medical record data from a fourth service unit, genomic record data from a fifth service unit, and clinical trials data from a sixth service unit, whereby the aggregation of the patient medical record data, genomic record data, and clinical trials data includes respectively determining one or more corresponding data standards managed by the fourth, fifth, and sixth service units and receiving the corresponding data from the fourth, fifth, and sixth service units in the determined one or more corresponding data standards, and the generated patient metadata includes the aggregated patient medical record data, genomic record data, and clinical trials data.

(5) The personalized biomedical information research analytics and knowledge discovery system of any one of (1) to (4), wherein the receiving exchange unit circuitry is further configured to transmit the patient metadata to the originating exchange unit based on a comparison of the patient metadata and the query criteria.

(6) The personalized biomedical information research analytics and knowledge discovery system of any one of (1) to (5), wherein the originating exchange unit circuitry is further configured to determine one or more of a proposed test, diagnosis, treatment, and personalized therapy, based on the received patient metadata.

(7) The personalized biomedical information research analytics and knowledge discovery system of any one of (1) to (6), wherein the originating exchange unit includes a memory that stores the received patient metadata.

(8) The personalized biomedical information research analytics and knowledge discovery system of any one of (1) to (7), wherein: the receiving exchange unit circuitry is further configured to tag the patient metadata with a corresponding patient identification code, and the patient identification code excludes Protected Health Information (PHI) as identified by the Health Insurance Portability and Accountability Act (HIPAA).

(9) The personalized biomedical information research analytics and knowledge discovery system of any one of (1) to (8), wherein the originating exchange unit circuitry is further configured to update the stored patient metadata when new patient metadata corresponding to the same patient identification code is received.

(10) The personalized biomedical information research analytics and knowledge discovery system of any one of (1) to (9), wherein the originating exchange unit determines the one or more of the proposed test, diagnosis, treatment, and personalized therapy, based on a longitudinal trend analysis of the stored patient metadata over a predetermined time period.

(11) A method of personalized biomedical information research analytics and knowledge discovery, the method comprising: transmitting, from an originating exchange unit to a receiving exchange unit, a query request including predetermined query criteria; aggregating, by the receiving exchange unit, protein-protein interaction data from a first service unit, wherein the aggregation includes determining one or more corresponding data standards managed by the first service unit and receiving the protein-protein interaction data from the first service unit in the determined one or more corresponding data standards; generating, by the receiving exchange unit in response to receiving the query request, patient metadata corresponding to the patient; transmitting, by the receiving exchange unit to the originating exchange unit, the patient metadata; and receiving, at the originating exchange unit from the receiving exchange unit, the patient metadata.

(12) The method of (11), further comprising: aggregating, by the receiving exchange unit, disease pathway data from a second service unit, whereby the aggregation of the disease pathway data includes determining one or more corresponding data standards managed by the second service unit and receiving the disease pathway data from the second service unit in the determined one or more corresponding data standards; and the generated patient metadata includes the aggregated disease pathway data.

(13) The method of (11) or (12), further comprising: aggregating, by the receiving exchange unit, therapeutics data from a third service unit, whereby the aggregation of the therapeutics data includes determining one or more corresponding data standards managed by the third service unit and receiving the therapeutics data from the third service unit in the determined one or more corresponding data standards; and the generated patient metadata includes the aggregated therapeutics data.

(14) The method of any one of (11) to (13), further comprising: aggregating, by the receiving exchange unit, patient medical record data from a fourth service unit, genomic record data from a fifth service unit, and clinical trials data from a sixth service unit, whereby the aggregation of the patient medical record data, genomic record data, and clinical trials data includes respectively determining one or more corresponding data standards managed by the fourth, fifth, and sixth service units and receiving the corresponding data from the fourth, fifth, and sixth service units in the determined one or more corresponding data standards; and the generated patient metadata includes the aggregated patient medical record data, genomic record data, and clinical trials data.

(15) The method of any one of (11) to (14), wherein the receiving exchange unit circuitry transmits the patient metadata to the originating exchange unit based on a comparison of the patient metadata and the query criteria.

(16) The method of any one of (11) to (15), further comprising: determining, by the originating exchange unit, one or more of a proposed test, diagnosis, treatment, and personalized therapy, based on the received patient metadata.

(17) The method of any one of (11) to (16), wherein: the originating exchange unit includes a memory that stores the received patient metadata, and the method further comprises tagging, by the receiving exchange unit, the patient metadata with a corresponding patient identification code, whereby the patient identification code excludes Protected Health Information (PHI) as identified by the Health Insurance Portability and Accountability Act (HIPAA); and storing the tagged patient metadata in the memory.

(18) The method of any one of (11) to (17), further comprising updating, by the originating exchange unit, the stored patient metadata when new patient metadata corresponding to the same patient identification code is received.

(19) The method of any one of (11) to (18), wherein the originating exchange unit determines the one or more of the proposed test, diagnosis, treatment, and personalized therapy, based on a longitudinal trend analysis of the stored patient metadata over a predetermined time period.

(20) A non-transitory computer readable medium having instructions stored therein that when executed by one or more processors causes the one or more processors included in an exchange unit to perform a method comprising: aggregating protein-protein interaction data from a first service unit, wherein the aggregation includes determining one or more corresponding data standards managed by the first service unit and receiving the protein-protein interaction data from the first service unit in the determined one or more corresponding data standards; generating, in response to receiving a query request transmitted from another exchange unit, patient metadata corresponding to the patient; and transmitting the patient metadata to the another exchange unit.

The invention claimed is:

1. A personalized biomedical information research analytics and knowledge discovery system comprising:
an originating personalized exchange unit including an originating personalized exchange unit processor and an originating personalized exchange unit memory, corresponding to a first patient; and
a receiving personalized exchange unit including a receiving personalized exchange unit processor and a receiving personalized exchange memory, corresponding to a second patient;
wherein:
the originating personalized exchange unit, implemented by the originating personalized exchange unit processor is configured to:
transmit, to the receiving personalized exchange unit, a query request including predetermined query criteria, and receive, from the receiving personalized exchange unit, personalized patient metadata corresponding to the second patient;

the receiving personalized exchange unit, implemented by the receiving personalized exchange unit processor, is configured to:

aggregate and integrate personalized protein-protein interaction data corresponding to the second patient from a first service unit comprising the personalized protein-protein interaction data to thereby generate personalized patient metadata for transmission to the originating personalized exchange unit, wherein the aggregation and integration of the personalized protein-protein interaction data includes determining the personalized protein-protein interaction data based on a plurality of disparate proteotypic data standards managed by the first service unit and receiving the personalized protein-protein interaction data from the first service unit, generate, in response to receiving the query request, the personalized patient metadata, and transmit, to the originating exchange unit, the personalized patient metadata;

wherein the generated personalized patient metadata includes the aggregated and integrated protein-protein interaction data; and the plurality of disparate proteotypic data standards comprise HL7, PSI-MI and MIAPE.

2. The personalized biomedical information research analytics and knowledge discovery system of claim 1, wherein:

the receiving personalized exchange unit processor is further configured to aggregate and integrate personalized disease pathway data corresponding to the second patient from a second service unit comprising the personalized disease pathway data, whereby the aggregation and integration of the personalized disease pathway data includes determining the personalized disease pathway data based on a plurality of disparate disease pathway data standards managed by the second service unit and receiving the personalized disease pathway data from the second service unit; and the generated personalized patient metadata further includes the aggregated and integrated personalized disease pathway data.

3. The personalized biomedical information research analytics and knowledge discovery system of claim 2, wherein:

the receiving personalized exchange unit processor is further configured to aggregate and integrate personalized therapeutics data corresponding to the second patient from a third service unit comprising the personalized therapeutics data, whereby the aggregation and integration of the personalized therapeutics data includes determining the personalized therapeutics data based on a plurality of disparate therapeutics data standards managed by the third service unit and receiving the personalized therapeutics data from the third service unit; and the generated personalized patient metadata further includes the aggregated and integrated personalized therapeutics data.

4. The personalized biomedical information research analytics and knowledge discovery system of claim 3, wherein:

the receiving personalized exchange unit processor is further configured to aggregate and integrate personalized patient medical record data corresponding to the second patient from a fourth service unit, personalized genomic record data corresponding to the second patient from a fifth service unit, and personalized clinical trials data corresponding to the second patient from a sixth service unit, whereby the aggregation and integration of the personalized patient medical record data, the personalized genomic record data, and the personalized clinical trials data includes respectively determining the personalized patient medical record data, the personalized genomic record data and the personalized clinical trials data based on a plurality of disparate corresponding patient medical record data standards, a plurality of disparate genomic record data standards and a plurality of disparate clinical trials data standards managed by the fourth, fifth, and sixth service units and receiving the corresponding the personalized patient medical record data, the personalized genomic record data and the personalized clinical trials data from the fourth, fifth, and sixth service units;

the generated personalized patient metadata includes the aggregated and integrated personalized patient medical record data, personalized genomic record data, and personalized clinical trials data.

5. The personalized biomedical information research analytics and knowledge discovery system of claim 1, wherein the receiving personalized exchange unit processor is further configured to transmit the personalized patient metadata to the originating personalized exchange unit based on a comparison of the personalized patient metadata and the predetermined query criteria.

6. The personalized biomedical information research analytics and knowledge discovery system of claim 1, wherein the originating personalized exchange unit processor is further configured to determine one or more of a proposed test, diagnosis, treatment, and personalized therapy, based on the received personalized patient metadata.

7. The personalized biomedical information research analytics and knowledge discovery system of claim 6, wherein the originating personalized exchange unit memory stores the received personalized patient metadata.

8. The personalized biomedical information research analytics and knowledge discovery system of claim 7, wherein:

the originating personalized exchange unit processor is further configured to tag the personalized patient metadata with a corresponding patient identification code, and the patient identification code excludes Protected Health Information (PHI) as identified by the Health Insurance Portability and Accountability Act (HIPAA).

9. The personalized biomedical information research analytics and knowledge discovery system of claim 8, wherein the originating personalized exchange unit processor is further configured to update the stored personalized patient metadata when new personalized patient metadata corresponding to the same patient identification code is received.

10. The personalized biomedical information research analytics and knowledge discovery system of claim 6, wherein the originating personalized exchange unit determines the one or more of the proposed test, diagnosis, treatment, and personalized therapy, based on a longitudinal trend analysis of the stored patient metadata over a predetermined time period.

11. The personalized biomedical information research analytics and knowledge discovery system of claim 1, wherein:

the personalized patient metadata comprises at least one selected from unstructured schema, unstructured data and semi-structured data;

the personalized protein-protein interaction data comprises at least biographic data, gene fusion, phylogenetic profiles, ortholog interaction, domain interaction and microarray gene co-expression corresponding to the second patient.

12. A computer-implemented method of exchanging personalized biomedical information, the method comprising:

transmitting, from an originating personalized exchange unit including an originating personalized exchange unit memory an originating personalized exchange unit processor that corresponds to a first patient to a receiving personalized exchange unit including a receiving personalized exchange unit processor and a receiving personalized exchange unit memory that corresponds to a second patient, a query request including predetermined query criteria;

aggregating and integrating, via the receiving personalized exchange unit processor, personalized protein-protein interaction data corresponding to the second patient from a first service unit comprising the personalized protein-protein interaction data to thereby generate personalized patient metadata for transmission to the originating personalized exchange unit, wherein the aggregation and integration includes determining the personalized protein-protein interaction data based on a plurality of disparate proteotypic data standards managed by the first service unit and receiving the personalized protein-protein interaction data from the first service unit generating, via the receiving personalized exchange unit processor, in response to receiving the query request, the personalized patient metadata corresponding to the second patient;

transmitting, via the receiving personalized exchange unit processor to the originating personalized exchange unit, the personalized patient metadata; and receiving, at the originating personalized exchange unit from the receiving personalized exchange unit, the personalized patient metadata;

wherein the generated personalized patient metadata includes the aggregated and integrated protein-protein interaction data; and the plurality of disparate proteotypic data standards comprise HL7, PSI-MI and MIAPE.

13. The computer-implemented method of claim 12, further comprising:

aggregating, via the receiving personalized exchange unit circuitry, personalized disease pathway data corresponding to the second patient from a second service unit comprising the personalized disease pathway data, whereby the aggregation of the personalized disease pathway data includes determining the personalized disease pathway data based on a plurality of disparate disease pathway data standards managed by the second service unit and receiving the personalized disease pathway data from the second service unit;

wherein the generated personalized patient metadata further includes the aggregated and integrated personalized disease pathway data.

14. The computer-implemented method of claim 13, further comprising:

aggregating and integrating, via the receiving exchange unit processor, personalized therapeutics data corresponding to the second patient from a third service unit comprising the personalized therapeutics data, whereby the aggregation and integration of the personalized therapeutics data includes determining the personalized therapeutics data based on a plurality of disparate therapeutics data standards managed by the third service unit and receiving the personalized therapeutics data from the third service unit;

wherein the generated personalized patient metadata further includes the aggregated and integrated personalized therapeutics data.

15. The computer-implemented method of claim 14, further comprising:

aggregating and integrating, via the receiving exchange unit processor, personalized patient medical record data corresponding to the second patient from a fourth service unit comprising the personalized patient medical record data, personalized genomic record data corresponding to the second patient from a fifth service unit comprising the personalized genomic record data, and personalized clinical trials data corresponding to the second patient from a sixth service unit comprising the personalized clinical trials data, whereby the aggregation and integration of the personalized patient medical record data, the personalized genomic record data, and the personalized clinical trials data includes respectively determining the personalized patient medical record data, the personalized genomic record data and the personalized clinical trials data based on a plurality of disparate patient medical record data standards, a plurality of disparate genomic record data standards and a plurality of disparate clinical trials data standards managed by the fourth, fifth, and sixth service units and receiving the personalized patient medical record, personalized genomic record data and personalized clinical trials data from the fourth, fifth, and sixth service units;

wherein the generated patient metadata includes the aggregated and integrated patient medical record data, genomic record data, and clinical trials data.

16. The computer-implemented method of claim 15, wherein the receiving personalized exchange unit transmits the personalized patient metadata to the originating personalized exchange unit based on a comparison of the personalized patient metadata and the query criteria.

17. The computer-implemented method of claim 15, further comprising:

determining, via the originating personalized exchange unit processor, one or more of a proposed test, diagnosis, treatment, and personalized therapy, based on the received personalized patient metadata.

18. The computer-implemented method of claim 17, wherein:

the originating personalized exchange unit memory stores the received personalized patient metadata, and the method further comprises:

tagging, via the originating exchange unit processor, the received personalized patient metadata with a corresponding patient identification code, whereby the patient identification code excludes Protected Health Information (PHI) as identified by the Health Insurance Portability and Accountability Act (HIPAA); and storing the tagged personalized patient metadata in the originating personalized exchange unit memory.

19. The computer-implemented method of claim 18, further comprising:

updating, via the originating exchange unit processor, the stored personalized patient metadata when new patient metadata corresponding to the same patient identification code is received.

20. The computer-implemented method of claim 15, wherein
the originating personalized exchange unit processor determines the one or more of the proposed test, diagnosis, treatment, and personalized therapy, based on a longitudinal trend analysis of the stored patient metadata over a predetermined time period.

21. The computer-implemented method of claim 12, wherein:
the personalized patient metadata comprises at least one selected from unstructured schema, unstructured data and semi-structured data;
the personalized protein-protein interaction data comprises at least biographic data, gene fusion, phylogenetic profiles, ortholog interaction, domain interaction and microarray gene co-expression corresponding to the second patient.

22. A non-transitory computer readable medium having instructions stored therein that when executed by one or more processors causes the one or more processors included in an exchange unit to perform a method comprising:
transmitting, from an originating personalized exchange unit including an originating personalized exchange unit memory an originating personalized exchange unit processor that corresponds to a first patient to a receiving personalized exchange unit including a receiving personalized exchange unit processor and a receiving personalized exchange unit memory that corresponds to a second patient, a query request including predetermined query criteria;
aggregating and integrating, via the receiving personalized exchange unit processor, personalized protein-protein interaction data corresponding to the second patient from a first service unit comprising the personalized protein-protein interaction data to thereby generate personalized patient metadata for transmission to the originating personalized exchange unit, wherein the aggregation and integration includes determining the personalized protein-protein interaction data based on a plurality of disparate proteotypic data standards managed by the first service unit and receiving the personalized protein-protein interaction data from the first service unit;
generating, via the receiving personalized exchange unit processor, in response to receiving the query request, the personalized patient metadata corresponding to the second patient;
transmitting, via the receiving personalized exchange unit processor to the originating personalized exchange unit, the personalized patient metadata; and
receiving, at the originating personalized exchange unit from the receiving personalized exchange unit, the personalized patient metadata;
wherein the generated personalized patient metadata includes the aggregated and integrated protein-protein interaction data; and
the plurality of disparate proteotypic data standards comprise HL7, PSI-MI and MIAPE.

23. The non-transitory computer readable medium of claim 22, wherein:
the personalized patient metadata comprises at least one selected from unstructured schema, unstructured data and semi-structured data;
the personalized protein-protein interaction data comprises at least biographic data, gene fusion, phylogenetic profiles, ortholog interaction, domain interaction and microarray gene co-expression corresponding to the second patient.

* * * * *